United States Patent [19]
Klainer et al.

[11] Patent Number: 5,780,251
[45] Date of Patent: Jul. 14, 1998

[54] ULTRASENSITIVE SINGLE-STEP, SOLID-STATE COMPETITIVE IMMUNOASSAY SENSOR WITH INTERFERENCE MODIFIER AND/OR GEL LAYER

[75] Inventors: Stanley M. Klainer; Stephen L. Coulter; Geoffrey F. Hewitt, all of Henderson, Nev.

[73] Assignee: FCI FiberChem, Inc., Las Vegas, Nev.

[21] Appl. No.: 774,389

[22] Filed: Dec. 30, 1996

Related U.S. Application Data

[63] Continuation-in-part of Ser. No. 671,378, Jun. 27, 1996.
[51] Int. Cl.⁶ .................. G01N 33/53; G01N 33/552
[52] U.S. Cl. .................. 435/7.93; 385/12; 385/129; 385/130; 422/55; 422/57; 422/82.05; 422/82.08; 422/82.09; 422/82.11; 435/287.1; 435/287.2; 435/287.9; 435/288.7; 435/808; 436/164; 436/172; 436/514; 436/518; 436/524; 436/525; 436/527; 436/805
[58] Field of Search .................. 385/72, 129, 130; 422/55, 57, 82.05, 82.08, 82.09, 82.11; 435/7.93, 287.1, 287.2, 287.9, 288.7, 808; 436/164, 172, 514, 518, 524, 525, 527, 528, 529, 535, 805

[56] References Cited

U.S. PATENT DOCUMENTS

| | | | |
|---|---|---|---|
| 5,082,630 | 1/1992 | Partin et al. | 422/82.08 |
| 5,242,828 | 9/1993 | Bergstrom et al. | 435/808 |
| 5,340,715 | 8/1994 | Slovacek et al. | 435/6 |
| 5,436,161 | 7/1995 | Bergstrom et al. | 435/808 |
| 5,512,492 | 4/1996 | Herron et al. | 436/518 |

*Primary Examiner*—Christopher L. Chin
*Attorney, Agent, or Firm*—Henry P. Sartorio

[57] ABSTRACT

Simplicity, sensitivity and versatility of optical sensors based on competitive immunoassays using antibody-antigen reactions are achieved by solid-state, single-step reactions which permit accurate sensitive qualitative and quantitative information to be obtained without human participation. All of the chemistry-biochemistry is an inherent part of the sensor. A direct reaction occurs when the sample (antigen) is brought in contact with the sensor. The sensitivity of the competitive immunoassay optical sensor is controlled and increased by selecting a tag for the antigen or altering the attachment of a tag to an antigen so that the binding of tagged antigen to an antibody is decreased relative to the binding of untagged antigen to the antibody. The user can vary size, molecular weight and geometric configuration of the tagged antigen. This can be accomplished by selecting the proper tag or by attaching the indicator material to the antigen through a spacer or by attaching the tag directly to the antigen and attaching a compound of proper molecular weight and size elsewhere. Pretreatment of the substrate to which the antibody-bound tagged antigen is immobilized to block the surface from unwanted interferences and the use of optical isolation increases sensitivity. If the tag cannot be attached to the antigen, it is attached to the antibody. Attaching the controlled size, molecular weight tag to either the antigen or antibody permits the analysis of species not normally measureable by competitive immunoassay, thus increasing the versatility of the method. Background from displaced tagged antigen can be reduced, and sensitivity increased, by including an interference modifier in the tagged antigen. A gel layer on the sensor extends the ability to detect gaseous or solid species by maintaining the sensing chemistry in an internal wet environment.

32 Claims, 24 Drawing Sheets

COMPARISON OF ANTIBODIES IN A COMPETITIVE IMMUNOASSAY

| | POLYCLONAL ANTIBODIES | AFFINITY-PURIFIED POLYCLONAL ANTIBODIES | MONOCLONAL ANTIBODIES | POOLED MONOCLONAL ANTIBODIES |
|---|---|---|---|---|
| SIGNAL STRENGTH | EXCELLENT | EXCELLENT | EXCELLENT | EXCELLENT |
| SPECIFICITY | GOOD, BUT SOME BACKGROUND | EXCELLENT | EXCELLENT | EXCELLENT |
| GOOD FEATURES | STABLE-MULTIVALENT INTERACTIONS | STABLE-MULTIVALENT INTERACTIONS | • SPECIFICITY<br>• HOMOGENEITY<br>• UNLIMITED SUPPLY | • STABLE-MULTIVALENT INTERACTIONS<br>• SPECIFICITY<br>• HOMOGENEITY<br>• UNLIMITED SUPPLY |
| BAD FEATURES | • LIMITED SUPPLY<br>• BACKGROUND | AVAILABILITY | NEED HIGH AFFINITY | NEED HIGH AFFINITY |

FIG. 1A

A COMPARISON OF SOME IMMUNOASSAY TECHNIQUES

| TYPE OF ANALYSIS | COMMON LABORATORY TECHNIQUES | | FIELD KITS | FCIE |
|---|---|---|---|---|
| | COMPETITIVE ASSAY | COMPETITIVE ASSAY | ELISA | COMPETITIVE ASSAY |
| SUBSTRATE | TEST TUBES/ MEMBRANE | MICROLITER PLATE | TEST TUBES | MEMBRANE/ CONTAINER/ WAVEGUIDE |
| SUITABILITY | LABORATORY | LABORATORY | LABORATORY/FIELD | LABORATORY/FIELD |
| NUMBER OF OPERATIONAL STEPS | 10 | 8 | 6 | 1 |
| PHYSICAL STATE OF SENSING CHEMISTRY/BIOCHEMISTRY | LIQUID | LIQUID | LIQUID | SOLID |
| PHYSICAL STATE OF SAMPLE WITHOUT EXTRACTION | LIQUID | LIQUID | LIQUID | SOLID/LIQUID |
| POSSIBILITY FOR HUMAN ERROR | HIGH | HIGH | MEDIUM | VERY LOW |
| SPECIFICITY | HIGH | HIGH | HIGH | HIGH |
| SENSITIVITY | PARTS-PER-BILLION | PARTS-PER-BILLION | PARTS-PER-BILLION | PARTS-PER-TRILLION |
| ANALYSIS TIME | > 20 MIN | > 20 MIN | ~20 MIN | ~3 MIN |
| QUANTITATIVE | SEMI | SEMI | SEMI | YES |
| REVERSIBLE | NO | NO | NO | NO/REGENERABLE |

FIG. 1C

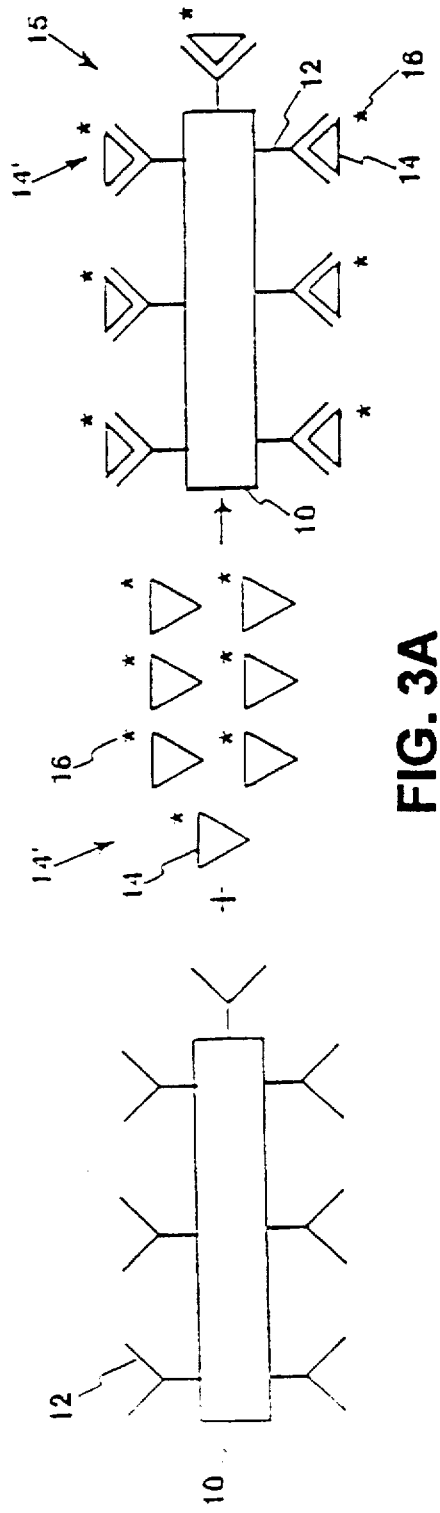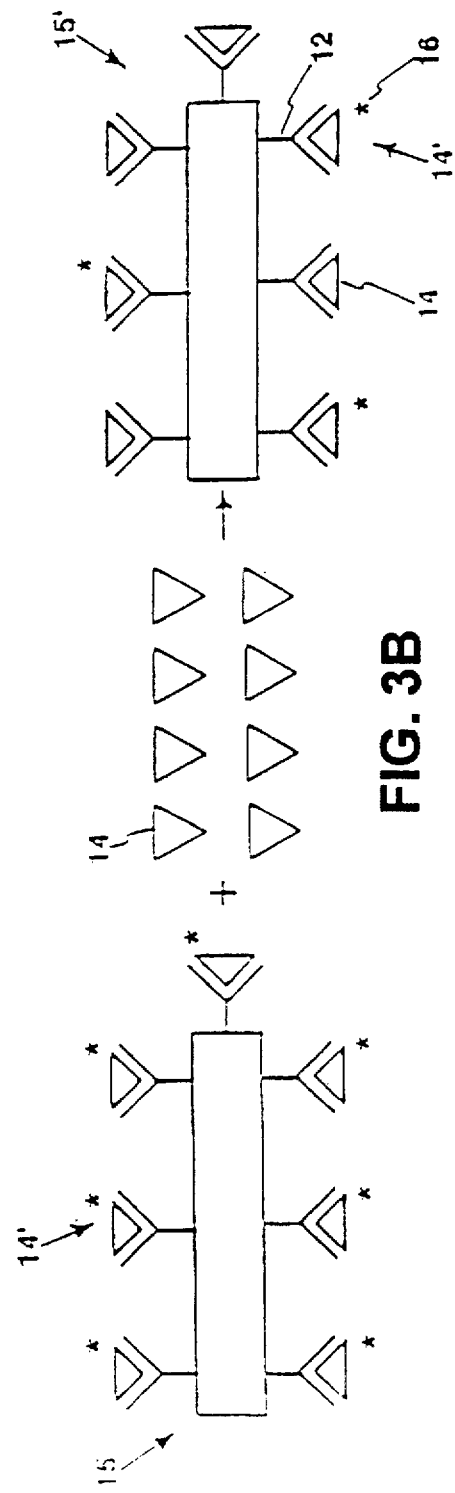
FIG. 3A
FIG. 3B

FITC = Fluorescein isothiocyanate

Fluoresceinthiocarbamyl ethylenediamine

ULTRASENSITIVE SINGLE-STEP, SOLID-STATE COMPETITIVE IMMUNOASSAY SENSOR WITH INTERFERENCE MODIFIER AND/OR GEL LAYER

RELATED APPLICATIONS

This application is a continuation-in-part (CIP) of U.S. patent application Ser. No. 08/671,378 filed Jun. 27, 1996.

BACKGROUND OF THE INVENTION

The invention relates generally to optical chemical and biochemical sensors and more particularly to solid-state sensors using single-step competitive immunoassays with antibodies. For the purposes of this invention the term sensor is used to include all single-step systems capable of doing a competitive immunological analysis where the optical output provides qualitative and quantitative information about the target molecule(s), i.e., sample. This invention improves the reaction efficiency and sensitivity of the solid-state, single-step competitive immunoassay sensing strategy of U.S. patent application Ser. No. 08/671,378.

In the single-step competitive immunoassay optical sensor described herein, an antibody is immobilized on the sensor substrate, and a tagged antigen is bound to the antibody. The tag is typically a fluorophore or chromophore. The target (untagged) antigen competitively binds to the antibody and displaces the tagged antigen, causing a change in sensor optical properties, e.g. fluorescence or color intensity, as the tag leaves the measurement field-of-view. The antibody-antigen reaction is used to identify the measured species and the change in optical properties can be directly related to the concentration of that species. U.S. Pat. No. 4,321,057 issued Mar. 23, 1983 to Buckles describes a fiber optic sensor based on competitive immunoassay between tagged and untagged antigen. It is also possible to adapt the solid-state, single-step immunoassay system so that it can be used with a radio-chemical tag.

Immunoassays have become a well accepted method of analysis in medicine because of their unquestionable specificity to the target compound of interest. If a monoclonal antibody is used, then its reaction is specific to a particular antigen (compound of interest). If, on the other hand, a polyclonal antibody is used, then its reaction is specific to a particular chemical structure rather than a precise chemical compound. A comparison of the types of antibodies suitable for the single-step, solid state competitive immunoassay are listed in Table 1 shown in FIG. 1A.

The use of immunoassays can be extended beyond basic medical applications to a variety of other analytical needs including environmental monitoring, process control, dosimetry/personal protection and military applications. There has, however, been reluctance to extend this technology to non-medical applications because of sensitivity considerations. The solid-state, single step technology described herein overcomes the sensitivity barrier and is not only applicable to all of the non-medical applications, but extends the number, types, efficiency and reliability for medical use while simplifying the analytical process.

The preferred state-of-the-art immunoassay techniques are enzyme-linked immunosorbent assay (ELISA) and enzyme-linked immuno-fluorescent assay (ELIFA) both of which are liquid systems based on the competition between sample analyte and analyte-enzyme conjugates for a limited number of antibody sites. These are multiple step chemical reactions which must be executed with precise timing for meaningful semi-quantitative measurements as shown in FIG. 1B.

The immunosensor technique described herein is also based on a competitive assay. It uses a new, unique single step biochemical approach which not only is much simpler than ELISA or ELIFA, but can be done in the solid state, i.e., no wet chemistry-biochemistry.

This invention primarily addresses comprehensive new approaches to competitive binding fluoro- and chromoimmunoassays. In particular it focuses on simplifying the analyses, optimizing the physical state of the sensor, improving sensitivity and making the sensor quantitative.

The competitive immunoassay of this invention reduces the number of individual analytical steps from an average of six (6) to ten (10) using ELISA or ELIFA to one (1) using this invention. A mechanism has been devised whereby all of the chemistry-biochemistry necessary to perform the detection, identification and quantification functions are inherently a part of the analytical strategy and all of the requisite data are easily accessed. A comparison of typical competitive immunoassay techniques appears in Table 2 shown in FIG. 1C.

The chemistry-biochemistry is innovative with respect to prior art in competitive immunoassays in that it is solid state, i.e., the need for, and use, of a liquid system has been obviated. Implementing previous strategies required that either a gas-liquid, liquid-liquid or solid-liquid measurement take place. The procedure is extended to gas-solid and solid-solid analyses using the innovative steps presented herein. The chemistry-biochemistry is immobilized directly on a substrate. This substrate can be of any configuration which permits an optical measurement to be made. Substrates include, but are not limited to, test tubes, cuvettes, fiber optics, optical waveguides, optical chips and optical waveguides on semiconductor chips. Membranes and test papers are also possible analytical surfaces.

While the sensor of the invention is a solid-state sensor, i.e. the user does not have to handle wet chemistry, the immunoassay reaction works best in a liquid environment. This is no problem when the sample is a liquid since the sample provides the liquid. However, it is a problem with gaseous or solid samples. Thus it is desireable to produce a solid-state sensor which has an internal liquid source. The use of water getting materials, such as lithium salts or absorbers, while possible water providers, is not considered viable in sensor applications because they are humidity dependent and add an unnecessary variable in water concentration to the system which directly affects reaction rate and the validity of the quantitative measurement.

Sensitivity is enhanced by reducing background contributions. The techniques of background reduction can only be used in the solid-state configuration where all of the components are affixed in a predetermined position and the number of uncontrolled parameters are minimized or completely eliminated. Background reduction is primarily accomplished by designing the chemical-biochemical system so that the fluorescent or chromophoric tag, which is ejected during the competitive step in the analysis, is either removed from the sensor or moved out of the field-of view of the optical (spectral) measurement.

Other methods of minimizing background include blocking the surface of the substrate so that nothing but the antibody can attach to it, assuring that the released tag is covalently bonded to the chemistry-biochemistry so that its motion is restricted to the point where it cannot participate in the analysis and using an optical isolation compound to diminish reflections from the sensor's surface.

The use of competitive antibody-antigen reactions has been primarily limited because of: (1) The need for liquid chemical-biochemical systems which inherently include all of the drawbacks and potential human errors associated with wet chemistry-biochemistry; (2) The use of multiple-step analysis—six (6) to ten (10) precise chemical-biochemical steps in a predescribed timed sequence; (3) Lack of sensitivity—high background noise, inadequate antibody loading on the substrate and inefficacious exchange between antibody bound to tagged antigen and untagged antigen and (4) The inability to measure small molecules—a requisite for many environmental, process control, and dosimeter applications.

For the molecules which can be measured using existing techniques such as ELISA, ELIFA or mass spectrometry the minimum detection limits (MDL) are, nominally between 35 and 50 parts-per-billion (ppb) and, in some cases as high as the low parts-per-million (ppm) range. The limit of quantification (LOQ) is a factor of 3.3 higher. These restrictions exclude their use in such important areas as: (1) Environmental monitoring, especially measuring pollutants to assure that drinking water, occupational health and safety, and Underwriter Laboratory (UL) standards are met; (2) Measuring contamination in chemical processes; (3) Examining personnel for alcohol, drug or other substances abuse; (4) Determining exposure to and presence of toxic substances and infectious diseases; and (5) Diagnosing and evaluating maladies such as cancer, heart infarctions, arthritis, gastrointestinal ailments, abnormal blood panels and urological problems. 5 ppb is the LOQ required for many of these applications which means that a MDL of 1.5 ppb is a requisite. The solid-state, single-step competitive immunoassay described herein has a MDL of less than 1.0 ppb (part-per-billion), and with potential to low ppt (part-per-trillion) or ppqd (part-per-quadrillion).

The production of solid-state, single-step, ultra high sensitivity competitive immunoassays for an extended list of antigens is the primary focus of this invention. This provides the ability to measure and quantify numerous antigens in the parts-per-million (ppm) to low parts per trillion (pptr) range irrespective of their molecular size. Thus the ability to measure extended dynamic concentration ranges and the analysis of small molecules are also parts of this invention.

As a result of the solid-state, single-step, high-sensitivity chemical-biochemical systems developed according to the present invention, the drawbacks that existing, prior art, immunoassays must be done by trained personnel and are subject to human error, are overcome. Specifically, the up-to-date prior art assays require mixing of chemicals, such as the addition of enzymes and dyes, in exact quantities and sequence, and at designated time intervals. The results, therefore, are only as accurate as the technician and are subject to the sum of all errors. The use of immunological systems, where there is no human participation in the chemistry-biochemistry, is an important part of this invention.

Optical waveguide chemical sensors (OWCS), optical waveguide biochemical sensors (OWBS), fiber optic chemical sensors (FOCS), fiber optic biochemical sensors (FOBS), optical chip chemical sensors (OCCS) and optical chip biochemical sensors (OCBS) as well as simple containers such as cuvettes, test tubes and bottles which can transmit an optical signal are all transducers in an information acquisition strategy which obtains real-time data about the presence and concentration of specific species, or chemical groups of compounds, in chemical and biochemical systems. In addition, the sensing substrate can be extended to membrane and test paper sensors which are amenable to optical measurements. Optical waveguides, which are a preferred sensing substrate, include flat channeled and non-channeled waveguides as well as chips with waveguides on them. Some waveguide sensor configurations are illustrated in FIGS. 2A–D as examples of typical substrates. These prior art configurations of waveguide, sensing chemistry, source, and detector arrangements can also be used to implement the present invention. FIG. 2A shows a typical waveguide configuration with sensor chemistry attached to a portion thereof, FIG. 2B shows more than one sensing chemistry on a single waveguide while FIG. 2C is a miniaturized waveguide which is totally covered with sensing chemistry. In order to have an internal reference, the waveguide can be half coated with the sensing chemistry-biochemistry and the second half left uncoated or coated with an unreactive surface and is used to obtain a reference signal, FIG. 2D.

Preferably the waveguide is half coated with the complete immobilization agent, sensing biochemistry and optional overcoatings, and the other half of the waveguide is coated with all but the sensing chemistry and is used to obtain a reference. In this configuration, in order to work, the inactive portion of the waveguide must face the illumination source and the reference signal must be taken before that of the coated section. A more practical arrangement is to use two (2) waveguides, sense and reference, illuminated by a single light source and the resultant signal detected by two (2) matched detectors. It is possible to use any of the configurations shown in FIGS. 2A, 2B and 2C in combination with a separate reference. In either arrangement the difference or ratio of the sense and reference signal contains the unadulterated concentration information. In the case of container-based sensors, the sensing chemistry is attached to the inner wall and the sample to be measured placed in the vessel. As with the waveguide sensors, sense and reference sensors can be employed either by using Lwo vessels, sense and reference, or by attaching both the sense and reference chemistries in the same container in a geometric arrangement that allows each chemistry to be interrogated individually. In the same procedure it is possible to coat membranes and test papers in a preselected geometric pattern to obtain sense and reference information.

Optical chemical and biochemical sensors are devices with indicators for preselected chemical and/or physical properties attached to their surfaces, so that sensitive, specific, real-time analyses can be made. These can be based on fluorescence, absorption, Raman, polarization, refraction, reflection or radiochemical measurements. The species or group-specific chemistry can be selected from organics, inorganics, metals, metallorganics, enzymes, monoclonal and polyclonal antibodies, biochemicals and polymers or combinations thereof. Interaction of an analyte with the sensing reagent (in this case a tagged antigen or tagged antibody) produces a change in one of the above mentioned spectroscopic parameters. For sensitive measurements using antibody-antigen reactions fluorescence, color, or polarization are the preferred measured properties depending on the molecular size of the target molecule. A readout device electronically converts light flux into voltage. Modulation in the voltage reading directly correlates with the analyte concentration.

FIGS. 3A,B show the basic reactions in a competitive immunoassay. The general reaction is the same for conventionally tagged antigen and for antigen tagged according to the present invention. In these Figures Y represents an antibody, *$\nabla$ (or $\nabla$*) is the tagged antigen and $\nabla$ is the untagged antigen, i.e., the target compound of interest. The greater the exchange rate between $\nabla$ and $\nabla$ the more sensitive the reaction. Ideally, most of the $\nabla$ will be lost at the actual (or integrated) concentration of the compound to be measured. This is not the case under normal circumstances; however, the present invention provides a method of making this happen.

FIG. 4A shows how an antibody (Y) is attached to a glass substrate and saturated with a tagged antigen (+∇). FIG. 5A shows the same arrangement on a membrane substrate. These arrangements are similar for conventionally tagged antigen and for antigen tagged according to the present invention.

SUMMARY OF THE INVENTION

It is an object of the invention to provide a solid-state, single-step competitive immunoassay.

It is also an object of the invention to increase sensitivity of a competitive immunoassay.

It is an added object of the invention to provide improved optical sensors based on competitive immunoassay.

It is a further object of the invention to provide a sensor which is capable of efficiently operating under gas-liquid, gas-solid, liquid-liquid, liquid-solid and solid-solid conditions.

It is another object of the invention to provide method and apparatus for competitive immunoassay which has sensitivity to pptr (part-per-trillion) or even ppqd (part-per-quadrillion) levels.

It is an additional object of the invention to provide sensors with a large dynamic range between ppm (part-per-million) and pptr.

It is a further object of the invention to provide a method for performing a competitive immunoassay for small molecules.

The invention is method and apparatus for competitive immunoassay having a tagged antigen bound to an antibody immobilized on a sensor substrate, in which the binding of the tagged antigen to the antibody is altered or distorted so that the untagged target antigen more easily displaces the tagged antigen. The binding of the tagged antigen is controlled by selecting a suitable large tag, or by making the tag larger by adding a long chain spacer to a smaller tag, or by making the tagged antigen larger and attaching a long chain elsewhere on the tagged antigen. The displaced tagged antigen is designed either to become a vapor when separated from the antibody or to have a specific affinity to the sensor's surface so that it is removed from the analytical field-of-view and does not represent unnecessary background which greatly affects sensitivity. Optical isolation is also provided. The antibody-tagged antigen is pretreated by a special washing technique. The sensor can be configured to detect a single antigen and multiple antigens, and can be placed on a variety of optical substrates including a chip, membrane or test paper. When the antigen cannot be tagged, the antibody can be tagged and a competitive immunoassay is still possible.

One aspect of the present invention obviates the need for a liquid system. It provides an environment whereby gas-solid and solid-solid reactions can take place. The surface of the sensor is dry, but the chemistry-biochemistry "appears wet" to the incoming target (sample) species. This is accomplished by adding "solid" water as an immobilized component of the sensing environment in the form of an aqua-gel or sol-gel. These gels act as solid-state reservoirs for water and can be designed to work as either a controlled leak or as a crushable water source. In the first approach water is continually added to the chemistry-biochemistry, thus keeping a known water concentration in the active part of the sensor, but not on the surface. Lifetime of solid state sensors of this type is dependent on the gel-water concentration and the size of the pores that generate the leak. In the second approach, water is not made available to the reaction until the gel is crushed. This provides both extended operational and shelf lives because the sensor is completely inert until the gels are broken and the water released. If sol-gels are used, providing a liquid reaction one is not limited to water, but to other solvents which can activate the requisite reaction and which are compatible with the sol-gel material. The aqua-gel and sol-gel containing sensors can also be used in water, thus eliminating the need for a different sensor for liquid vs. solid measurements.

Another aspect of the present invention addresses maintaining a high sensitivity system for gas (vapor)-solid and solid-solid reactions by minimizing the contribution of the ejected tag. The ejected tag is designed to be removed from the analytical system because there is no freedom to move it out of the field of view. This requires modifying the tagged antigen that is used to load the antibody on the sensor so that it is in vapor form or so that it will be immobilized on the sensor surface when it is supplanted by the untagged antigen.

BRIEF DESCRIPTION OF THE DRAWINGS

FIG. 1A is Table 1 comparing antibodies in a competitive immunoassay.

FIG. 1C is Table 2 comparing prior art competitive immunoassay techniques to the present invention.

FIGS. 3A,B illustrate the basic reactions of a competitive immunoassay.

DETAILED DESCRIPTION OF THE PREFERRED EMBODIMENTS

FIGS. 2A–D illustrate various waveguide sensor embodiments of the invention. While the general configuration of waveguide, sensing region, source, detector is similar to the prior art, the antigen is tagged in accordance with the invention, as described herein. Thus the source, detector and other aspects of the sensors are conventional, but the sensors also incorporate the inventive features described herein to form new sensors.

Figure 1B:
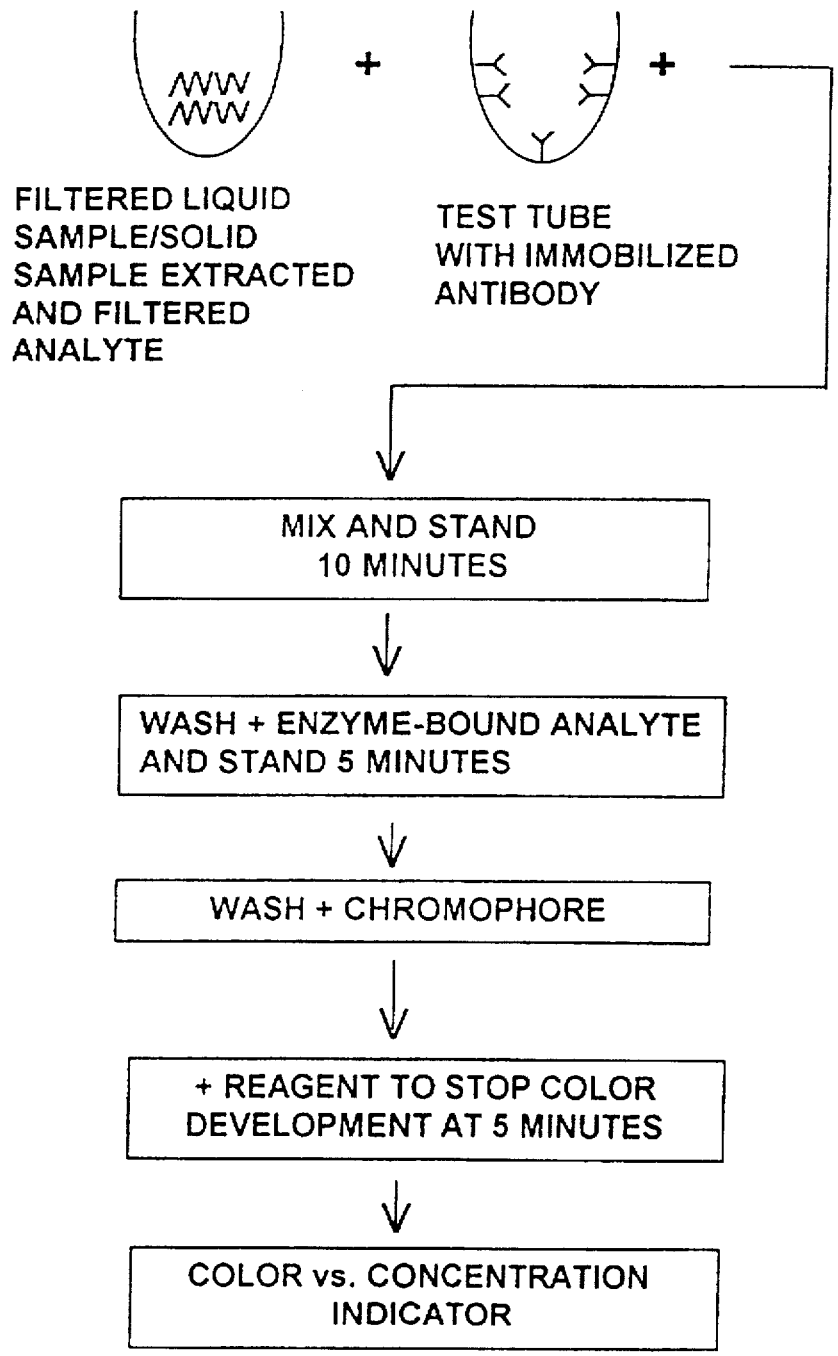
FIG. 1B illustrates the prior art for competitive immunoassays.
Figure 2A:
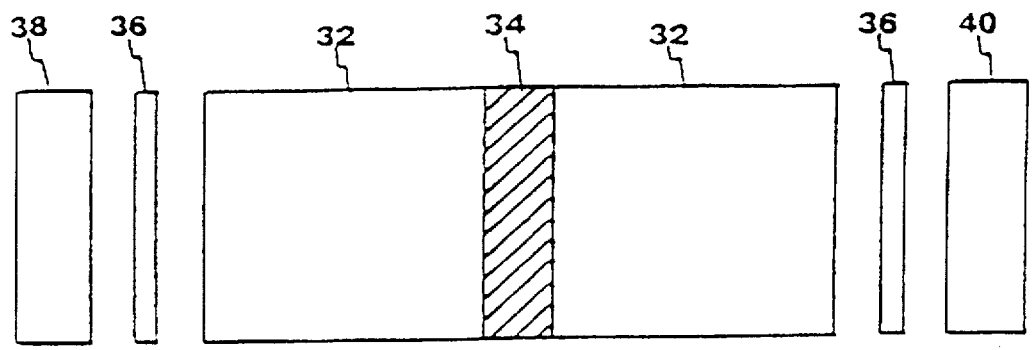
FIGS. 2A–D illustrate waveguide sensor configurations with single and multiple sensing chemistries.
Figure 2B:
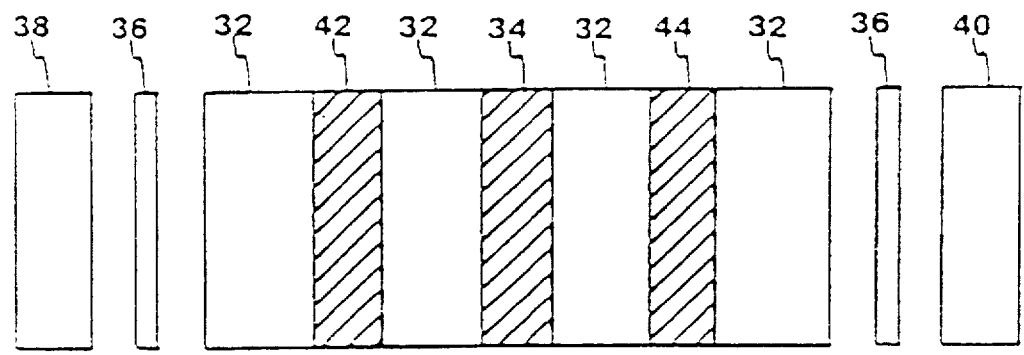
Figure 2C:
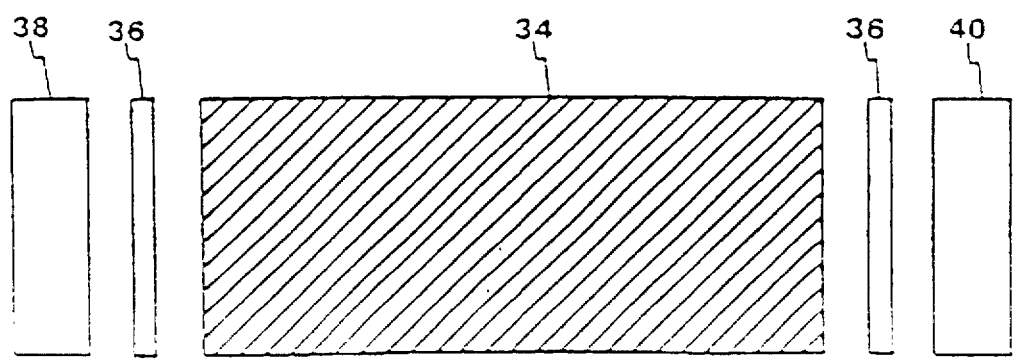
Figure 2D:
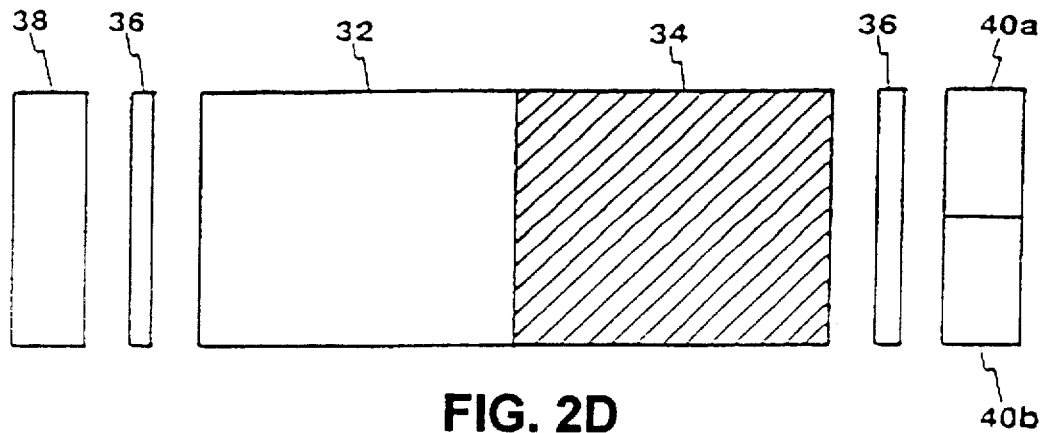

As shown in FIG. 2A, a waveguide 32 is positioned between a source 38 and a detector 40 with filters 36. A sensing region 34 made up of an immobilized antibody with bound tagged antigen is formed on waveguide 32. FIG. 2B illustrates a multi-sensor configuration where additional sensing regions 42,44 are added to waveguide 32. Each sensing region 42,44 is made up of a different immobilized antibody with associated bound tagged antigen. The tags are different so the responses can be differentiated. In FIG. 2C, sensing region 34 covers the entire waveguide, which can be a miniaturized structure, e.g. a chip as described in U.S. Pat. No. 5,439,647 which is herein incorporated by reference. The configuration of FIG. 2C can be modified to provide an internal reference as shown in FIG. 2D by coating only half the waveguide 32 with sensing region 34. The uncoated waveguide 32 is closest to source 38. A pair of detectors 40a, 40b are used to separately measure the reference signal and optical signal from sensing region 34.

Figure 2E:
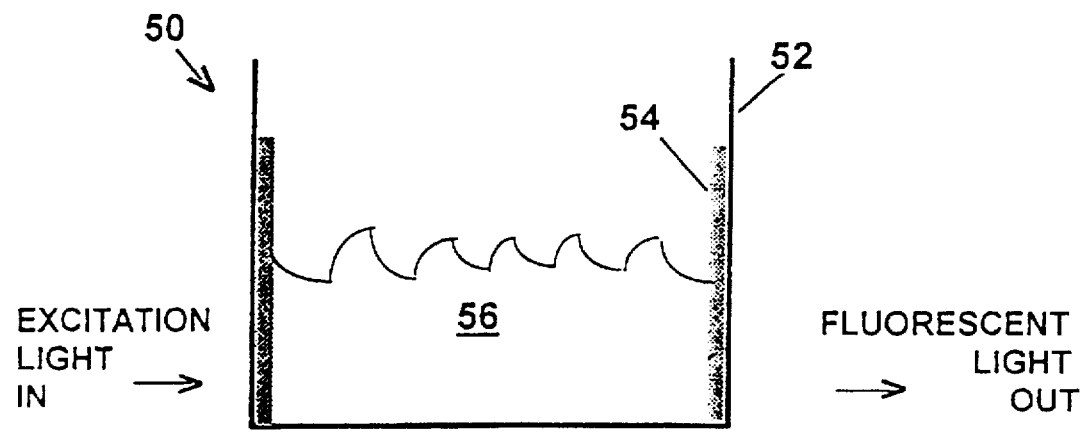
FIG. 2E illustrates a sensor arrangement in a container.
Figure 4A:
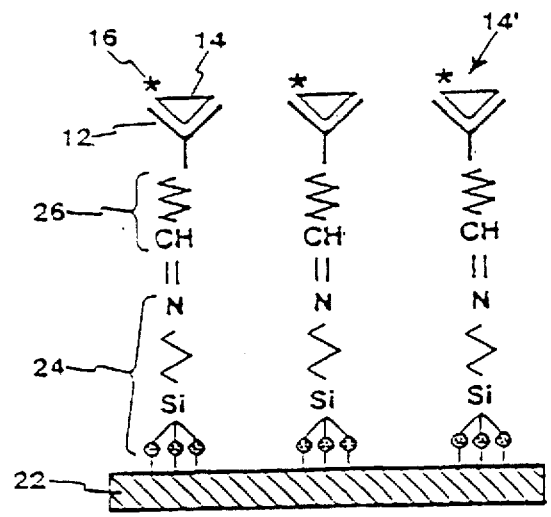
FIGS. 4A–C illustrate tagged antigen bound to an antibody attached to a glass or waveguide substrate.
Figure 4B:
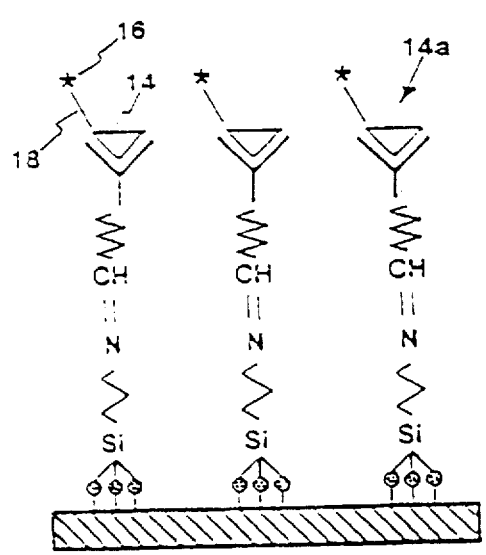
Figure 4C:
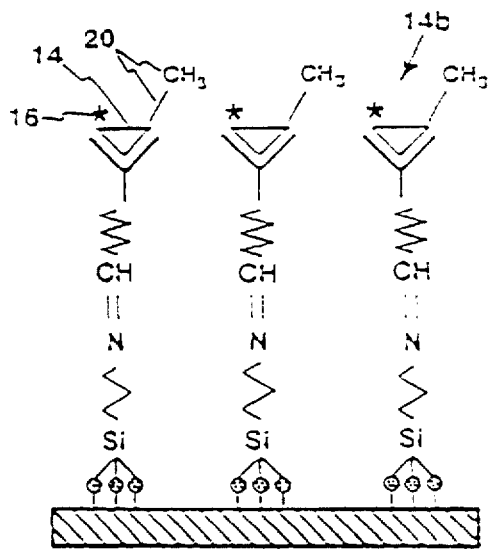
Figure 4D:
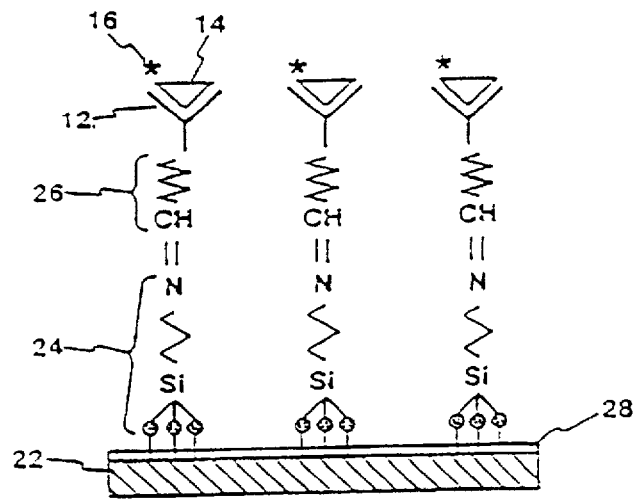
FIGS. 4D–F are the systems of FIGS. 4A–C including an additional optical isolation layer.
Figure 4E:
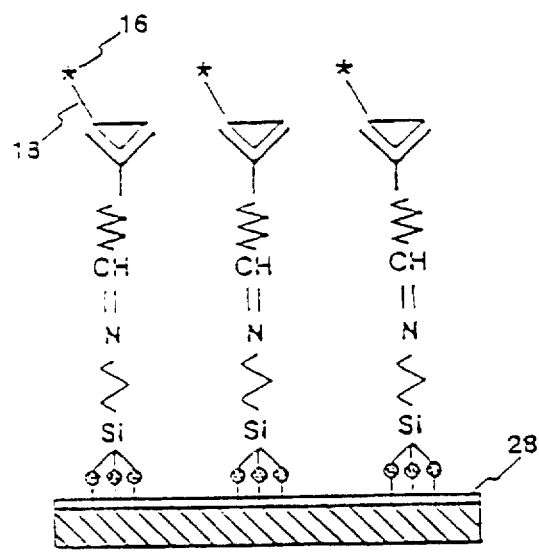
Figure 4F:
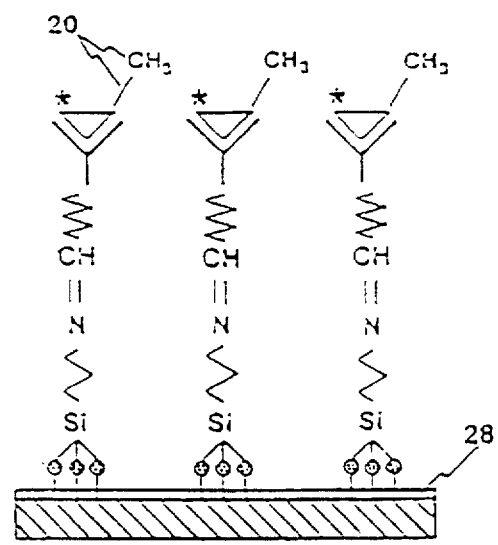
Figure 5A:
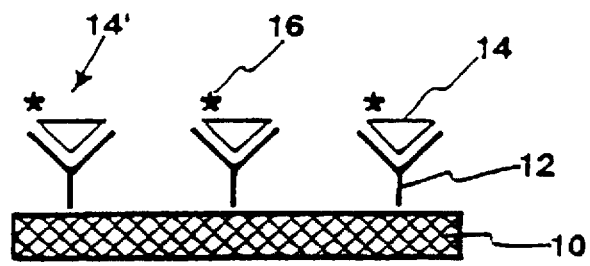
FIGS. 5A–F are similar arrangements as FIGS. 4A–F on a membrane substrate.
Figure 5B:
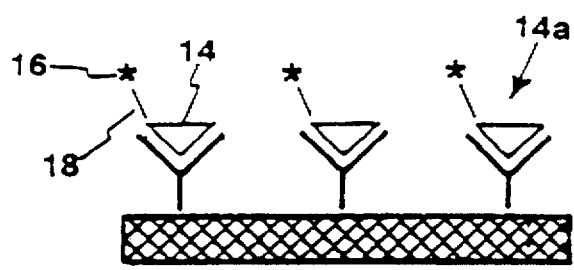
Figure 5C:
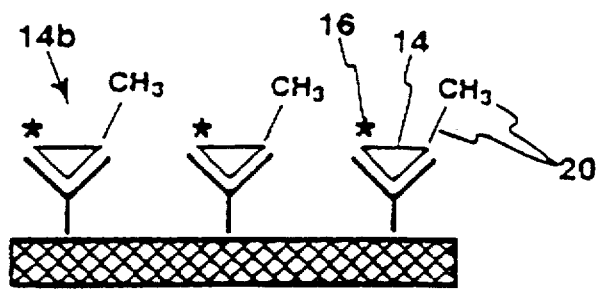
Figure 5D:
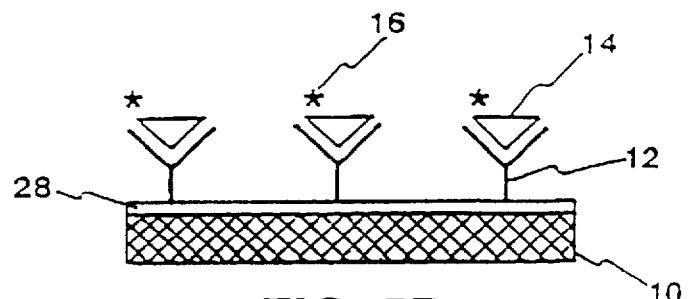
Figure 5E:
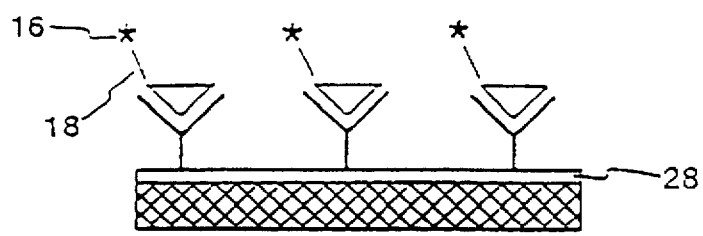
Figure 5F:
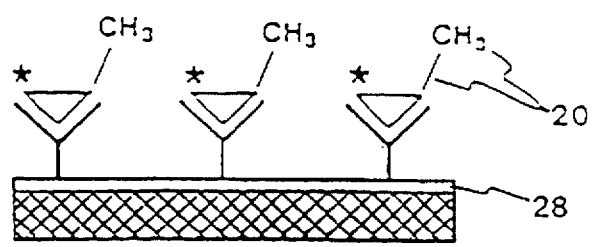

An alternate embodiment of a single step solid state competitive immunoassay sensor 50, as shown in FIG. 2E, is formed of a cuvette, test tube, bottle or similar container 52. Sensor 50 includes a coating 54 on at least one inner wall of container 52. Coating 54 is similar to those previously described for the waveguide embodiments i.e. an immobilized antibody with affinity controlled tag which has been tailored to a desired sensitivity level. In operation, an aqueous sample 56 is added to container 52 where it interacts with the solid state chemistry-biochemistry (coating) 54. The change in optical properties of coating 54 can be measured through container 52 using conventional instrumentation. For example, if the tag is a fluorescent tag, excitation light can be input and a fluorescent signal can be measured.

The basic reactions in a competitive immunoassay are illustrated in FIGS. 3A,B. The reactions are basically the same whether the antigens are conventionally tagged or tagged according to the invention. A substrate 10 with antibodies 12 immobilized thereon is contacted with a solution containing tagged antigen 14' which is composed of antigen 14 with attached tag 16. The tagged antigen 14' binds to the antibody 12, producing sensor 15. When sensor 15 is brought into contact with a sample containing antigen 14, antigen 14 competes with tagged antigen 14' for binding sites on antibody 12. Antigen 14 displaces tagged antigen 14' producing sensor 15' which has different optical characteristics than sensor 15. The sensitivity of sensor 15 will be determined by the ease with which antigen 14 can competitively displace tagged antigen 14'. The invention alters the binding of tagged antigen 14' so that antigen 14 more easily displaces tagged antigen 14'. Substrate 10 may be an optical fiber or other waveguide structure, or other support through which a light signal may be input and output to measure changes in sensor 15.

Since the interaction between an antibody and antigen is a "lock-and-key" fit, i.e. only one (1) antigen will react with a monoclonal and only (1) chemical structure will react with a polyclonal, it is necessary to come up with an approach whereby the tagged antigen is sufficiently distorted so that its ability to bind with the antibody is impaired but not negated. On the other hand, the binding between $^+\nabla$ and the antibody must be strong enough so that it cannot be removed except by an antigen which makes a better fit, i.e. $\nabla$, the specific analyte of interest.

There are three (3) approaches for distorting $^{+}\nabla$, i.e., making $^{+}\nabla$ of suitable size to decrease binding relative to $\nabla$: (1) a large tag is selected so that the tagged antigen has sufficient size, FIGS. 4A, 5A; (2) a long-chain, high molecular weight compound (spacer) can be placed between the antibody and the tag as shown in FIGS. 4B and 5B; and (3) a simple tagging compound is used and a long-chain high molecular weight compound can be attached elsewhere on the antigen, FIGS. 4C and 5C. In either case it is important to use a "distorting compound" which does not change the shape of the antigen to the point where it is not recognized by the antibody.

As shown in FIGS. 4A, 5A, tagged antigen 14' formed of antigen 14 with attached tag 16, binds to antibody 12 which is immobilized on a substrate. In FIG. 4A, antibody 12 is attached to a glass or waveguide substrate 22 by a silane 24 and glutaraldehyde 26. In FIG. 5A, antibody 12 is directly attached to membrane substrate 10. The same methods are used to immobilize the antibody 12 to the substrate in FIGS. 4B–C, 5B–C. Since the tagged antigen differs from the untagged antigen in the presence of the tag, proper selection of a suitably sized tag, if one is available, can produce a tagged antigen with the requisite decreased binding to the antibody.

If a suitable tag is not available, then the invention can be implemented with available tags by changing the tagged antigen to alter the relative binding strength compared to untagged antigen. As shown in FIGS. 4B,5B, tagged antigen 14a is formed by attaching tag 16 to antigen 14 through a long chain high molecular weight compound 18. Alternatively, as shown in FIGS. 4C, 5C, tagged antigen 14b is formed by attaching tag 16 directly to antigen 14, but additionally attaching a long chain high molecular weight compound 20 elsewhere on antigen 14. Compound 20 can also be used to change the vapor pressure or affinity of the tag.

Although the sample will generally be liquid, solid samples can also be detected. If the surface of the substrate is modified, so it can scrape a solid surface and transfer a sample to the sensing chemistry-biochemistry, then a solid-solid analytical reaction can take place and qualitative and quantitative information obtained. In most situations the solid-solid reaction can be initiated with the single-step, solid-state chemistry as previously described. In special cases, however, it may be necessary to keep the surface of the sensor wet (water or solvent) to initiate the reaction or to increase the solid-solid interaction. In these cases a selective absorbing species is added to the solid-state chemistry. This retains and acts as a reservoir for the desired wetting agent and releases it as needed during the analysis.

An additional aspect of the invention is providing a solid state sensor with an internal liquid reaction zone to enhance gas-solid and solid-solid reactions. The liquid, usually water or water-buffer, is provided in the form of a gel, e.g. aqua-gel or sol-gel, and immobilized to the substrate as a part of the sensor.

Figure 6:
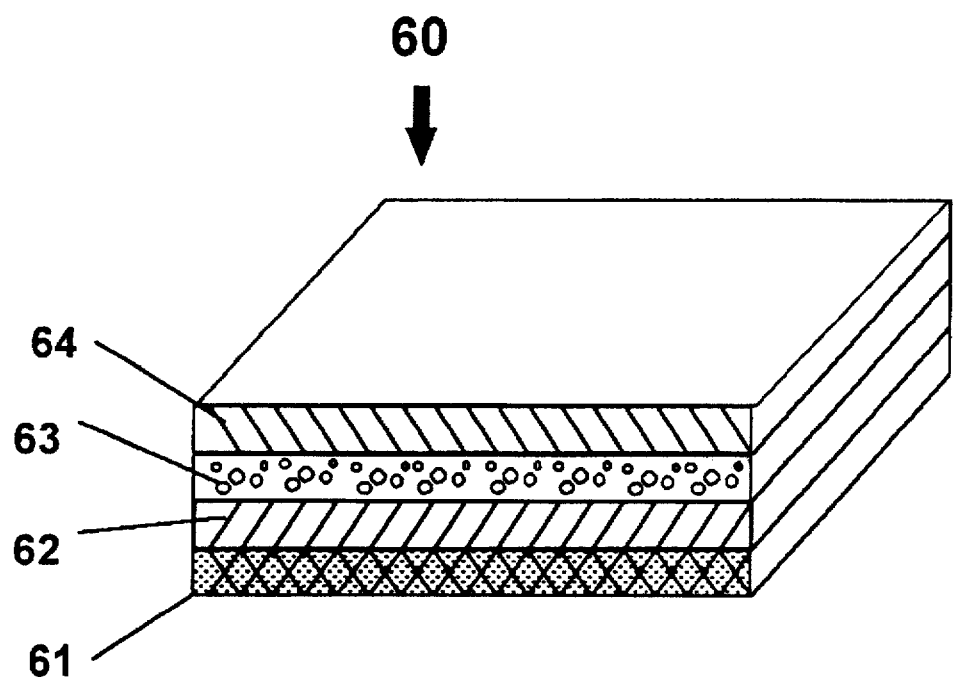
FIG. 6 is a view of a solid-state sensor with internal liquid source.

An illustrative view of a solid state sensor structure which maintains the sensing chemistry in an internal liquid environment to improve the ability to detect gaseous or solid species is shown in FIG. 6. Sensor 60 is formed on a substrate 61. Immobilization chemistry 62 attaches the sensing chemistry formed of antibodies with tagged antigen (or alternatively tagged antibodies) to substrate 60. Immobilization chemistry 62 also attaches the gel material which provides the internal liquid source to the sensor 60. Thus the sensing chemistry/gel layer 63 contains the sensing chemistry and the gel material which surrounds or is in intimate contact with the sensing chemistry. The gel material is preferably intermixed with the sensing chemistry but may also be in layers above and below. An optional protective overcoating 64, which is permeable to the sample, or which is broken before use of the sensor, can be placed over the sensor 60. The gel material contains or encapsulates water, buffer, or other solvent to maintain the sensing chemistry in an internal wet environment. The gel material is in the form of beads or capsules which contain the liquid. The sensing chemistry/gel layer 63 is permeable to the sample, so that untagged antigen can contact the sensing chemistry and displaced tagged antigen can pass through. The gel material, e.g. beads or capsules, may be sufficiently porous so that a controlled amount of the incorporated liquid leaks and is continuously in contact with the sensing chemistry or it may be non-porous so that the sensing chemistry is kept dry until the gel material is crushed by application of external pressure to release the fluid into contact with the chemistry. The continuously leaking gel embodiment will generally have a shorter shelf life than the breakable embodiment.

Figure 7A:
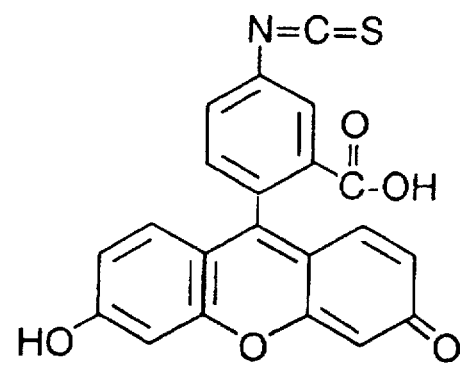
FIGS. 7A–B are the chemical formulas of a pair of representative fluorescein based fluorescent tags.
Figure 7B:
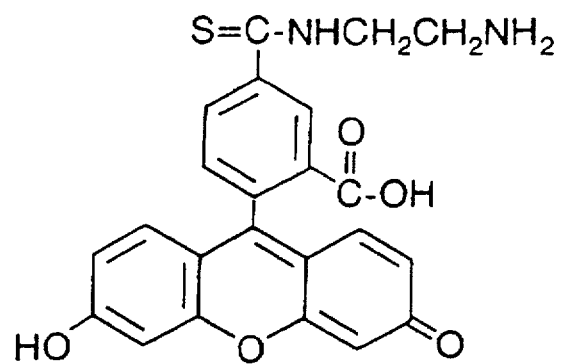
Figure 8A:
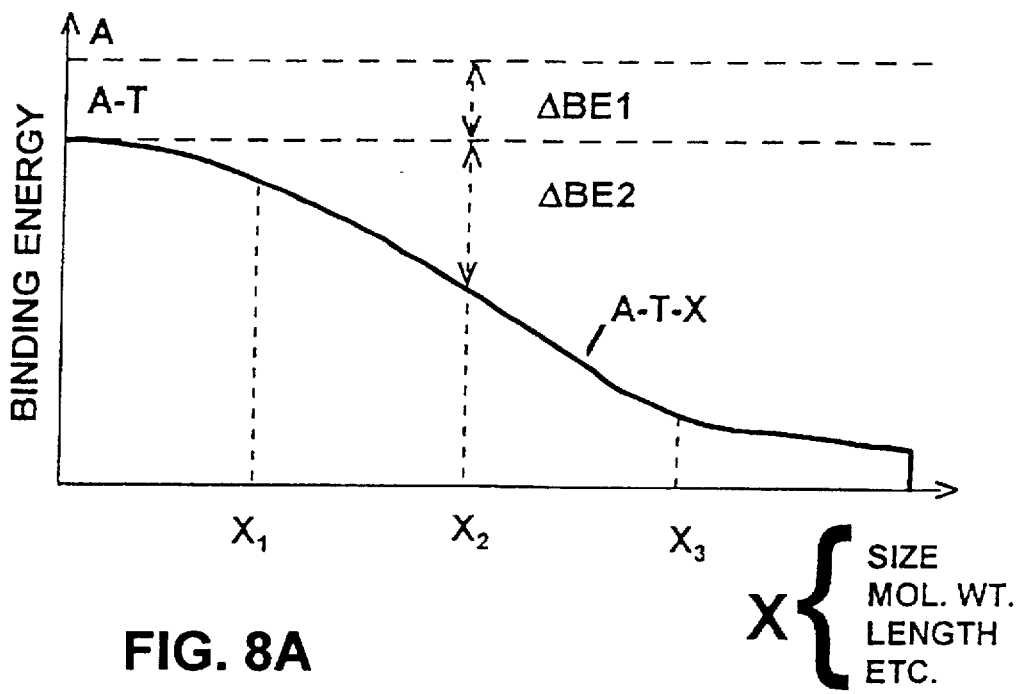
FIGS. 8A–B illustrates principles of affinity control of a tagged analyte as related to binding energy and sensitivity.
Figure 8B:
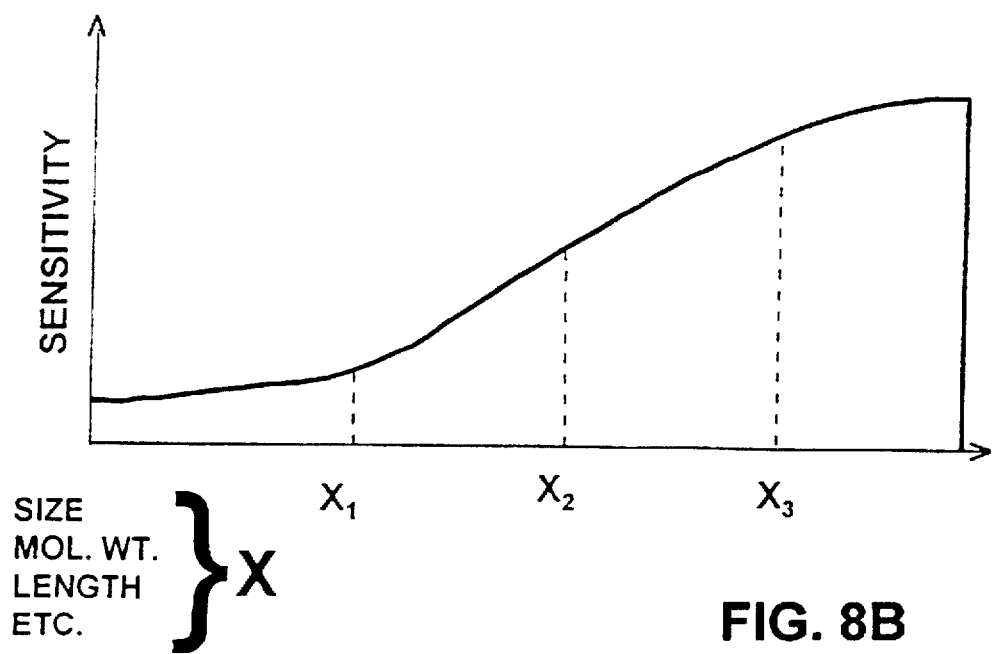

From the standpoint of simplicity and reproducibility, the use of a tagging compound which also distorts the antigen is the best approach, i.e., the use of a suitably large tag. This means that only one (1) synthetic operation has to be performed on the antigen. For example, if cocaine, morphine or heroin are the antigens, they cannot be measured below 1 ppm when the simple tag. fluorescein isothiocyanate (FITC), FIG. 7A, is used. If fluorescein-thiocarbamyl ethylenediamine is used, FIG. 7B, then 160 ppb of cocaine can be detected, FIG. 9. Note that this compound has a higher molecular weight than the FITC and also has a distortion chain. Thus the tag provides both the indicator (fluorescein) and the distorting compound. This tag was selected because it distorted the antigen to make the exchange between $^+\nabla$ and $\nabla$ optimum. If only FITC had been available, it could have been attached to the antigen through a long chain compound, or it could have been attached directly to the antigen and another chemical group(s) attached elsewhere on the tag. The choice of tags which distort the antigen are made based on experimental data. Each tag must be selected based on the antigen to which it is being attached.

In cases where the target antigen cannot be tagged, i.e. the target compound has no active group to which a tag can be attached, then it is necessary to tag the antibody, as further described below. The tags are based on an active indicator material, e.g., a fluorophore, which is preferably a laser dye because of its high quantum efficiency. Illustrative compounds suitable for tags for antigens include, but are not limited to:

fluoresceinthiocarbamyl ethylenediamine rhodamine B isothiocyanate eosin-5-isothiocyanate malachite green isothiocyanate rhodamine X isothiocyanate Lissamine™ rhodamine B sulfonyl chloride 6-carboxyrhodamine 6G hydrochloride 5-(and-6)-carboxy-X-rhodamine 6-(fluorescein-5-(and -6)-carboxamido)hexanoic acid succinimidyl ester Texas Red® sulfonyl chloride Other tags can be found in Handbook of Fluorescent Probes and Research Chemicals, 5th ed., 1992–1994, Richard P. Haugland, Molecular Probes, Inc., which is herein incorporated by reference.

The tag is selected, or attached to the antigen through additional compounds, or additional compounds are attached to the antigen, to produce ideally the lowest binding energy of the tagged antigen to the antibody so that the tagged antigen does not come off unless the untagged antigen is present, but the tagged antigen is easily displaced by the untagged antigen. Although the ideal lowest binding energy may not be achieved, significant reduction of the binding energy of the tagged antigen will greatly increase sensitivity to untagged antigen. By following the principles of the invention, suitable tagged antigen can be produced by routine experimentation.

The ejected tag, as discussed in U.S. patent application Ser. No. 08/671,378 is designed so that, in a liquid system, it moves out of the field-of-view of the measurement system and does not act as a background which could interfere with the tag - no tag measurement. This, however, is only possible in a liquid system where there are enough degrees of freedom for the tag to be mobile and move away from the measurement area. This movement is not available in gas (vapor)-solid and solid-solid situations.

An additional aspect of the invention addresses maintaining a high sensitivity system for gas (vapor)-solid and solid-solid reactions by minimizing the contribution of the ejected tag. In this case the ejected tag must be removed from the analytical system because there is no freedom to move it out of the field of view. This requires modifying the tagged antigen that is used to load the antibody on the sensor. The modifier can be used in two (2) ways:

(1) The modifier can be used to increase the vapor pressure of the ejected tag so that it becomes a vapor and it leaves the surface of the sensor. This can be accomplished, for example, by use of a trimethyl silyl compound, i.e., $(CH_3)_3SiCl$ where the —Cl moiety is used to attach the modifier to the tag. This results in even greater sensitivity than the liquid system since the tag, which represents background, is completely removed and the noise in the signal to noise ratio is minimized.

(2) The modifier can be used to provide a group specific site so that the ejected tag is immediately trapped and immobilized on the surface of the sensor out of the optical path. The modifier contains an active group or moiety such as —Cl as a point of attachment. In this approach it is necessary to match refractive indices of the individual components so that light does not interact with the ejected, collected tag.

Adding the modifier to the tag system will require adjustments in the spacer, the tag or both in order to retain the desired bond strength.

In summary, according to the invention, affinity control of a (fluorescent or other) tagged analyte is performed to control the sensitivity of a single step solid state competitive immunoassay. The invention controls the differential binding energy between an untagged antigen (target analyte) A and a tagged antigen A-T to an antibody Ab which is immobilized on a solid state sensor. A sensor that is saturated with tagged antigen, Ab:A-T, is contacted with a sample containing untagged antigen A. If the untagged antigen has a higher binding energy to the antibody that the tagged antigen, A will displace A-T, producing a sensor with Ab:A, which has different optical properties. The lower the binding energy of A-T compared to A, the more sensitive the sensor.

According to the invention, an affinity controlled tagged analyte A-T-X is produced, using an affinity controller X, which lowers the binding energy to the antibody Ab (compared to A-T) and the solid state sensor with immobilized antibody Ab is saturated with the affinity controlled tagged analyte, Ab:A-T-X. When the saturated solid state sensor is placed in contact with a sample containing the untagged analyte A, the analyte A more easily displaces the affinity controlled tagged analyte, i.e. Ab:A-T-X+A→Ab:A+ A-T-X more strongly than Ab:A-T+A→Ab:A+A-T. Thus the affinity controller X can be utilized to increase the sensitivity of the solid state competitive immunoassay by changing the binding energy of the tagged analyte in a controlled manner.

Further, according to the invention, an affinity controlled tagged analyte A-T-Y-M is produced where Y is an affinity controller component and M is an interface modifier component which assures that the ejected tag and its components do not contribute to background. Thus the affinity controller X is formed of Y-M which lowers the binding energy to the antibody Ab (compared to A-T). In the solid state sensor, immobilized antibody Ab is saturated with the partially affinity controlled tagged analyte, Ab:A-T-Y. The modifier, M, is attached after Ab:A-T-Y is formed because A-T-Y-M will be a vapor or will be reactive with the substrate. The principles of the invention relating to affinity control of the tagged antigen still apply. The affinity controller X is designed using a combination of components Y and M.

Thus, when the saturated solid state sensor is placed in contact with a sample containing the untagged analyte A, the analyte A more easily displaces the affinity controlled tagged analyte, i.e. Ab:A-T-Y-M+A→Ab:A+A-T-Y-M more strongly than AB:A-T+A→Ab:A+A-T. Thus the affinity controller component Y and the interference modifier component M can be utilized to increase the sensitivity of the solid state competitive immunoassay by changing the binding energy of the tagged analyte in a controlled manner.

The effects are illustrated in FIG. 8A which plots the binding energy of the various forms of the analyte (untagged, tagged, affinity controlled tagged) as a function of some parameter of the affinity controller X. Since Y-M is designed to be X when elimination of interference effects is desired, FIG. 8A is also representative of the modified sensor. To perform the competitive immunoassay, the binding energy of the untagged analyte A must be greater than the tagged analyte A-T, and the difference ABEl determines the sensitivity. If the sensitivity is not great enough for a particular tag T, then the affinity controllers X or Y-M can be used to reduce binding energy and increase sensitivity. The binding energy will decrease as a measurable function of the size, molecular weight, chain length, etc. For example, for a particular affinity controller $X_2$, the binding energy is decreased by ABE2 from the binding energy of A-T. Thus the total difference in binding energy is the sum of ΔBE1+ ΔBE2. Thus the user can determine a range of values of X, e.g. $X_1$ and $X_3$, which provide desired levels of sensitivity for any particular antibody/antigen for any particular application. In a similar manner affinity controllers $(Y-M)_1$, $(Y-M)_2$----→$(Y-M)_n$ can be selected. A plot of sensitivity as a function of X (or Y-M) is shown in FIG. 8B.

In the affinity controlled tagged analyte A-T-X or A-T-Y (which will subsequently be modified to A-T-Y-M), the affinity controlled tags T-X or T-Y can take many different forms. T-X or T-Y may be a compound T' based on or containing T. T-X or T-Y may be a combination of tag-spacer where the tag T is connected to analyte A by means of X or Y. T and X or T and Y may also be separately attached to A at different sites. In all forms, for a particular antibody and analyte which binds to the antibody, and a particular tag T, a user can produce various forms of A-T-X or A-T-Y by selecting different affinity controllers X or Y, e.g. different size, molecular weight, chain length, and measure the binding energies and sensitivity levels produced, using routine experimental techniques. Once A-T-Y is bound to the antibody, M is added as described previously. In making these selections it is desirous that X and Y-M be as similar as possible.

The background noise, which reduces the signal to noise ratio of a measurement can come from four (4) sources: (1) Unused active sites on the substrate, (2) Interference from the ejected tagged antigen, (3) Reflections and light scattering from the substrate, and (4) Loose tags on the antibody or antigen.

The easiest first step to sensitivity is to make sure that the tagging compound is present only when attached to either the antigen or antibody. In the conventional method of tagging this is no problem since no effort is made to reduce the bond strength between *∇ and ∇ and traditional washing techniques suffice. When the bond between the antibody and *∇ is deliberately weakened, it is necessary to use milder washing techniques, e.g. neutral buffer and triply distilled water. Washing is done repetitively until there is absolutely no indication of fluorescence in the used wash solution. This washing treatment to remove loose tags forms an additional part of the invention.

Two (2) approaches are used to make sure there are no unused active sites on the substrate to which interfering compounds can attach: (1) The substrate is allowed to react with the antibody containing the tagged antigen for an extended period of time (hours to days). This assures that the maximum number of antibodies are attached to the substrate. (2) The remaining sites are bound to an inert blocking compound such as bovine serum albumin (BSA). This is required because geometric and steric hindrances do not allow all the active sites to be bound to antibody. Examples of other blocking agents are blotto, blotto/tween, tween and horse serum. These examples are not intended to be all inclusive or a limitation; any compound that can block unused sites can be used.

To assure that the expelled tagged antigen does not interfere in a liquid system, the total ejected chemical system must remain intact, as shown in brackets ([ ]) in Equation 1A.

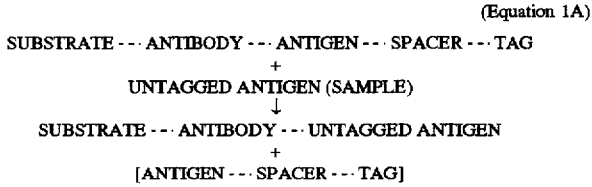
(Equation 1A)

SUBSTRATE - - - ANTIBODY - - - ANTIGEN - - - SPACER - - - TAG

+

UNTAGGED ANTIGEN (SAMPLE)

↓

SUBSTRATE - - - ANTIBODY - - - UNTAGGED ANTIGEN

+

[ANTIGEN - - - SPACER - - - TAG]

The requirements for a completely solid-system are different in that not only does the ejected tag system have to stay intact, but it must also leave the analysis zone as shown in equation 1B.

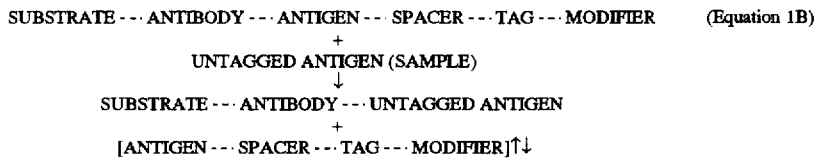

SUBSTRATE - - - ANTIBODY - - - ANTIGEN - - - SPACER - - - TAG - - - MODIFIER (Equation 1B)

+

UNTAGGED ANTIGEN (SAMPLE)

↓

SUBSTRATE - - - ANTIBODY - - - UNTAGGED ANTIGEN

+

[ANTIGEN - - - SPACER - - - TAG - - - MODIFIER]↑↓

This is accomplished by the inclusion of an interface modifier in the tagged system, as described above. If the antigen-spacer-tag or antigen-large tag or antigen-tag-chemical group remain intact, the discharged tag is excluded from the vicinity of the sensor both by size (steric hindrance) and weight in the liquid system, or vaporization or immobilization in the solid system and is eliminated as a background interference. In Equation 1B, ↑↓ is a combination of ↑, vaporization, and ↓, immobilization, to show that the modifier can be selected to perform either function. Also the antigen from the tagged antigen cannot interfere with the antigen in the sample. Converting the tag system to a vapor can be done in liquid as well as solid systems. It is the preferred method in that it is the only approach that guarantees complete elimination of the tag and thus background generated by the tag.

When a spacer is used it will be an organic compound such as a polymer or oligomer. The spacer must meet several criteria: (1) It must contain functional groups which allow it to form chemical bonds between itself and the antigen and itself and the tag, (2) It must fit between the antigen and the tag without causing steric hindrances (getting in the way) which would prevent, or hinder, the tagged antigen from reaching the antibody, (3) It (or a combination of the spacer and the tag) must distort the tagged antigen sufficiently so that the antibody-antigen (sample) bond is stronger than the antibody-tagged antigen bond. This is important so that the competition can not only take place, but the untagged antibody is the preferred reaction.

The antibody—antigen—spacer—tag, or antibody—antigen—spacer—tag—modifier, is chosen so that there is a weak, but stable bond between the antibody and tagged antigen, so that there is optimum exchange with the untagged antigen. Adding the modifier changes this bond strength and this must be compensated for either by changing the spacer or tag or both, as discussed previously.

Reflections and light scattering from the substrate are normally handled using spectroscopic techniques, i.e. using a narrow slit or narrow band filter to sort the excitation light (reflected and scattered) from the fluorescence emission signal. In order to get maximum sensitivity, however, it is necessary to use wide slits or broad band filters to collect as much light as possible so as to enhance light collection. Since spectral sorting cannot be used, two (2) ways to handle this problem have been invented for solid substrates: (1) The substrate can be given a matted (i.e., frosted or opaque for glass) finish to reduce the scattering and reflections from the excitation light and (2) an inert non-reflecting compound, such as charcoal, can be added to the blocking agent or the substrate to render the substrate "flat black" and non-reflective, FIGS. 4D–F. It is imperative that the addition of charcoal or other optical isolation follow the immobilization of the antibody (with bound tagged antigen) or the active sites will be blocked and no (or minimum) antibody will be attached to the substrate. In the case of the membrane substrate, only the use of charcoal or other optical isolation is possible since pretreatment would destroy the membrane, FIGS. 5D–F. For both types of substrate the non-reflecting compound can be added at any compatible step in the chemistry after immobilization. FIGS. 4D–F, 5D–F show the addition of an optical isolation layer 28 to the structures of FIGS. 4A–C, 5A–C.

The optical isolation layer can be of a variety of materials. The optical isolation can be a dispersion of a black, white, red or reflective material in an inert and antigen-permeable polymer. Examples for colored materials include carbon black, barium sulfate, titanium dioxide, red or black ferrous oxide, gold particles, or glimmer pigments. In addition to BSA, antigen-permeable polymers into which the colored materials are dispersed include silicone, polystyrene or ethyl cellulose. As shown schematically and not to scale in FIGS. 4D–F, 5D–F, the antibodies extend far beyond the optical isolation layer. However, the optical isolation layer which is formed on the substrate will typically cover the antibodies but allow passage of the antigen. The optical isolation layer may also form a non-reflective surface below the antibody binding sites.

The solid-state, single-step competitive immunoassay sensor is shown in its entirety, from U.S. patent application Ser. No. 08/671,378, in Equation 2A and is the resultant reaction between the sensor and a target antigen (sample).

(Equation 2A)

BLOCKING AGENT

|

SUBSTRATE - - - ANTIBODY - - - ANTIGEN - - - SPACER - - - TAG

|

OPTICAL ISOLATOR

+

UNTAGGED ANTIGEN (SAMPLE)

↓

BLOCKING AGENT

|

SUBSTRATE - - - ANTIBODY - - - UNTAGGED ANTIGEN

|

OPTICAL ISOLATOR

+

[ANTIGEN - - - SPACER - - - TAG]

The additional features of the invention, as described herein, which greatly improve the efficiency and sensitivity are shown in Equation 2B.

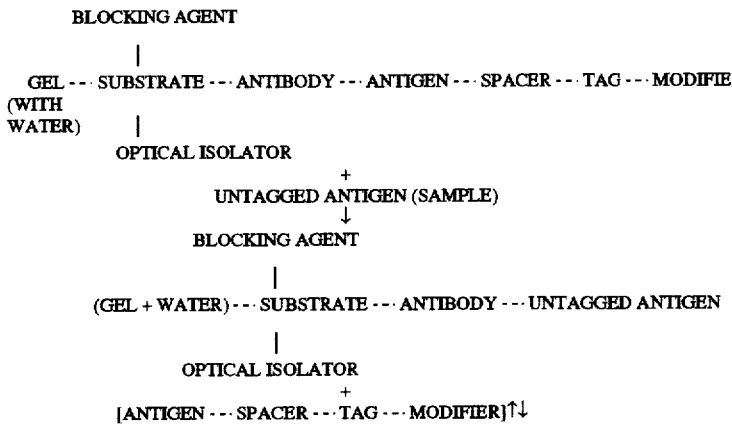

(Equation 2B)

Figure 9:
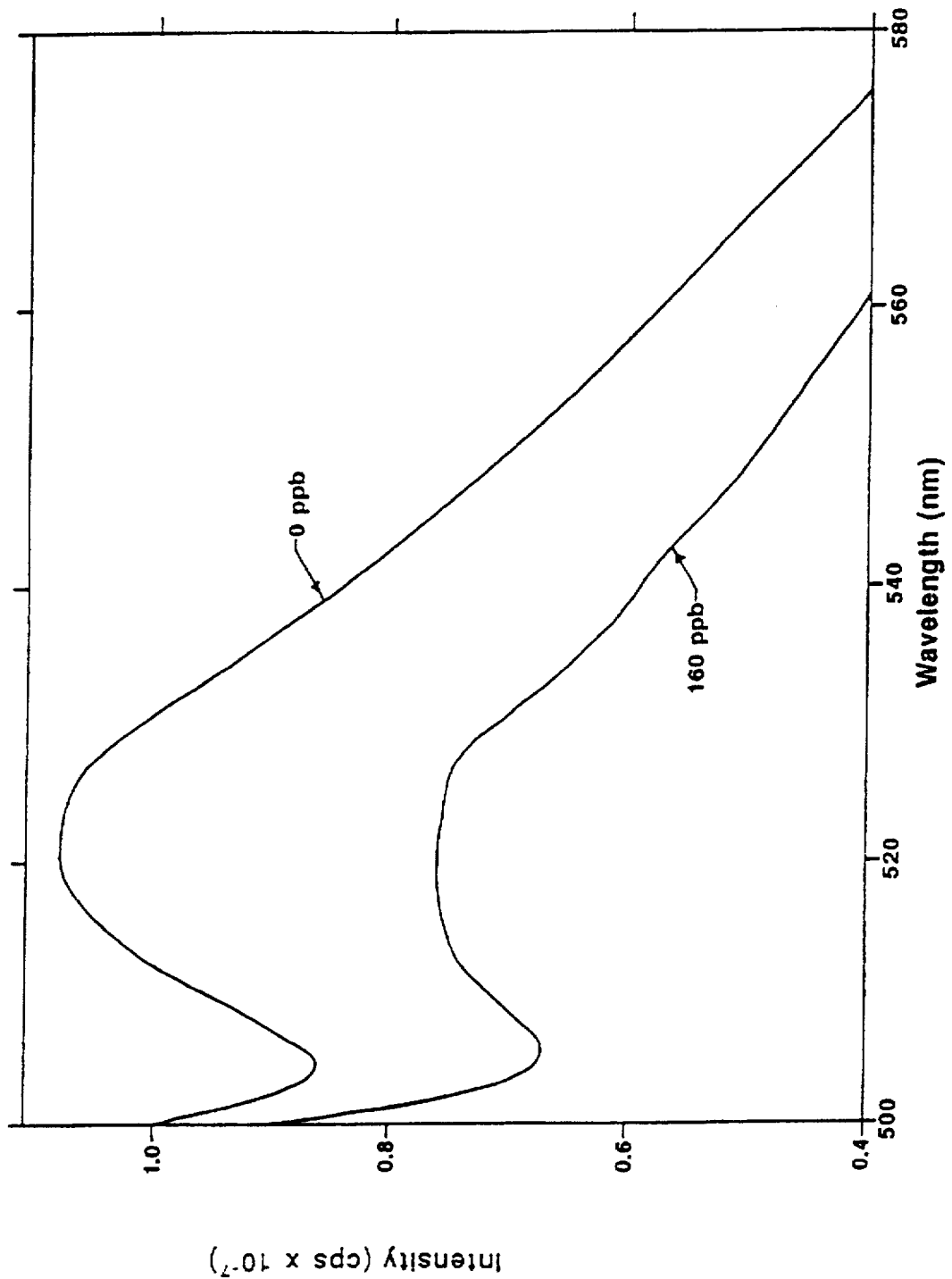
FIG. 9 shows the fluorescent spectrum of a sensor using the tag of FIG. 7B with no cocaine and with 160 ppb cocaine.
Figure 10:
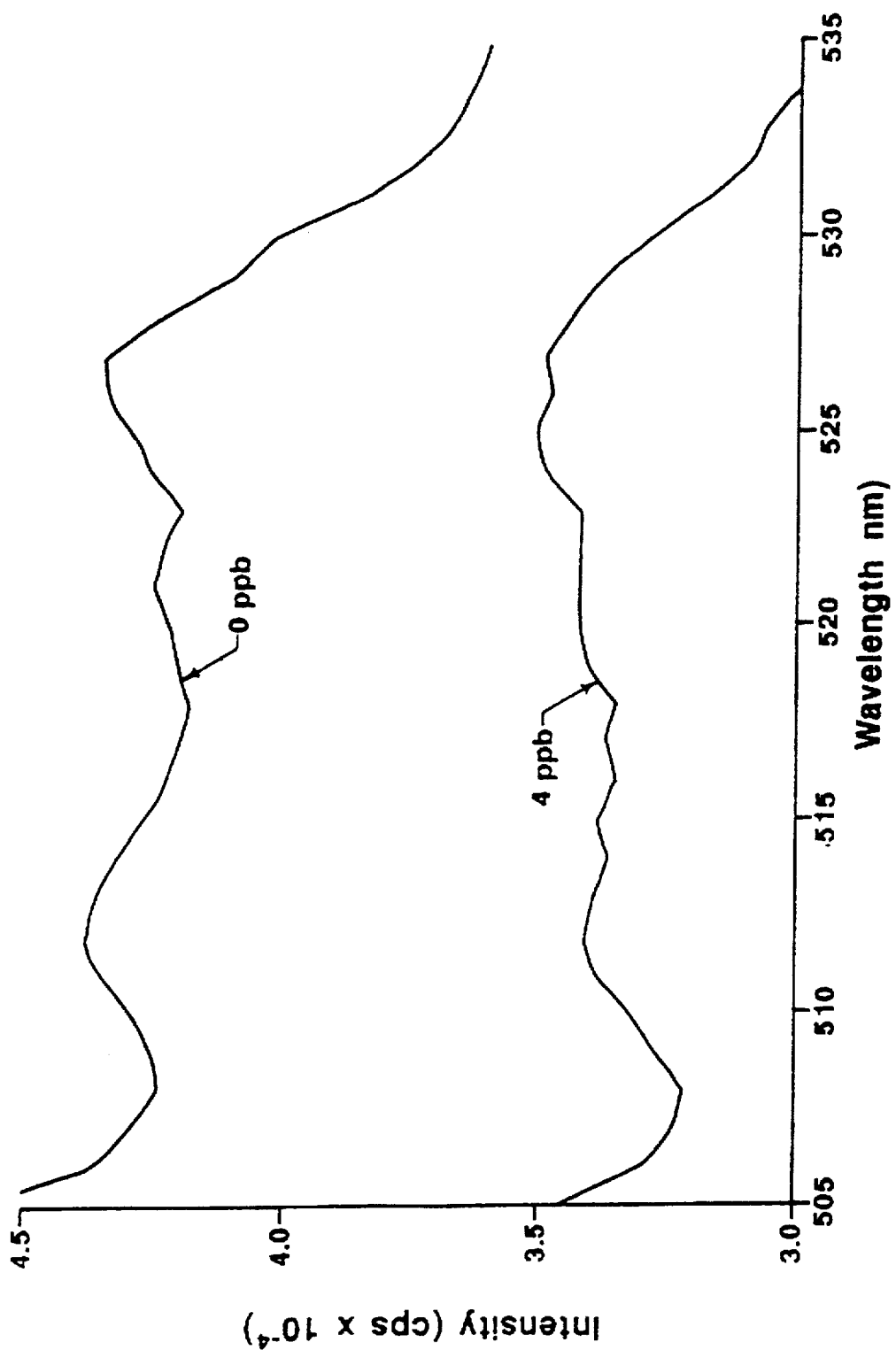
FIG. 10 shows the fluorescent spectrum of a sensor using the tag of FIG. 7B, optical isolation, and special washing, with no cocaine and with 4 ppb cocaine.
Figure 11:
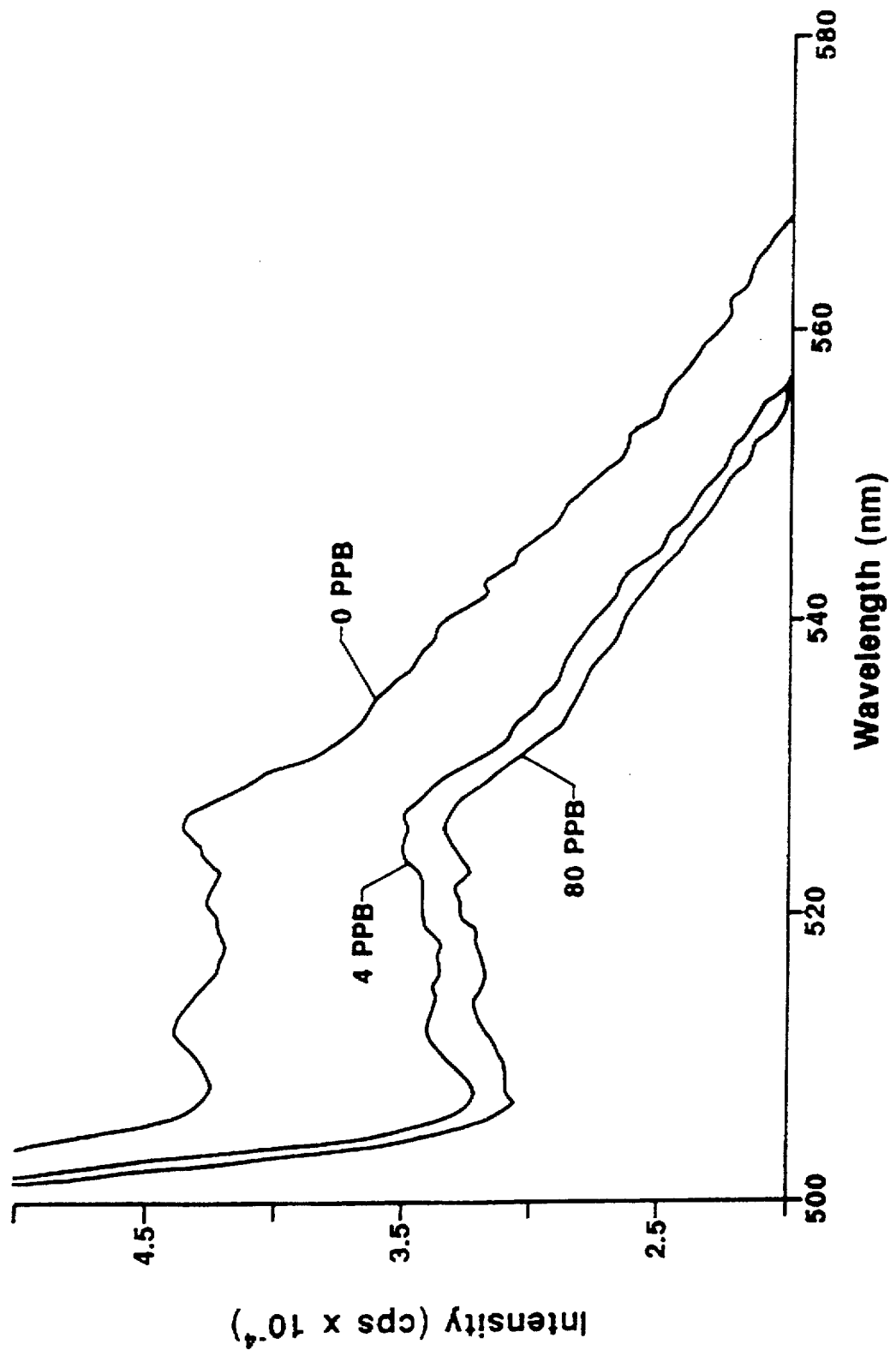
FIG. 11 shows another fluorescent spectrum as in FIG. 10, showing that the sensor is most sensitive between 0 and 4 ppb cocaine and that saturation is reached at approximately 80 ppb cocaine.
Figure 12:
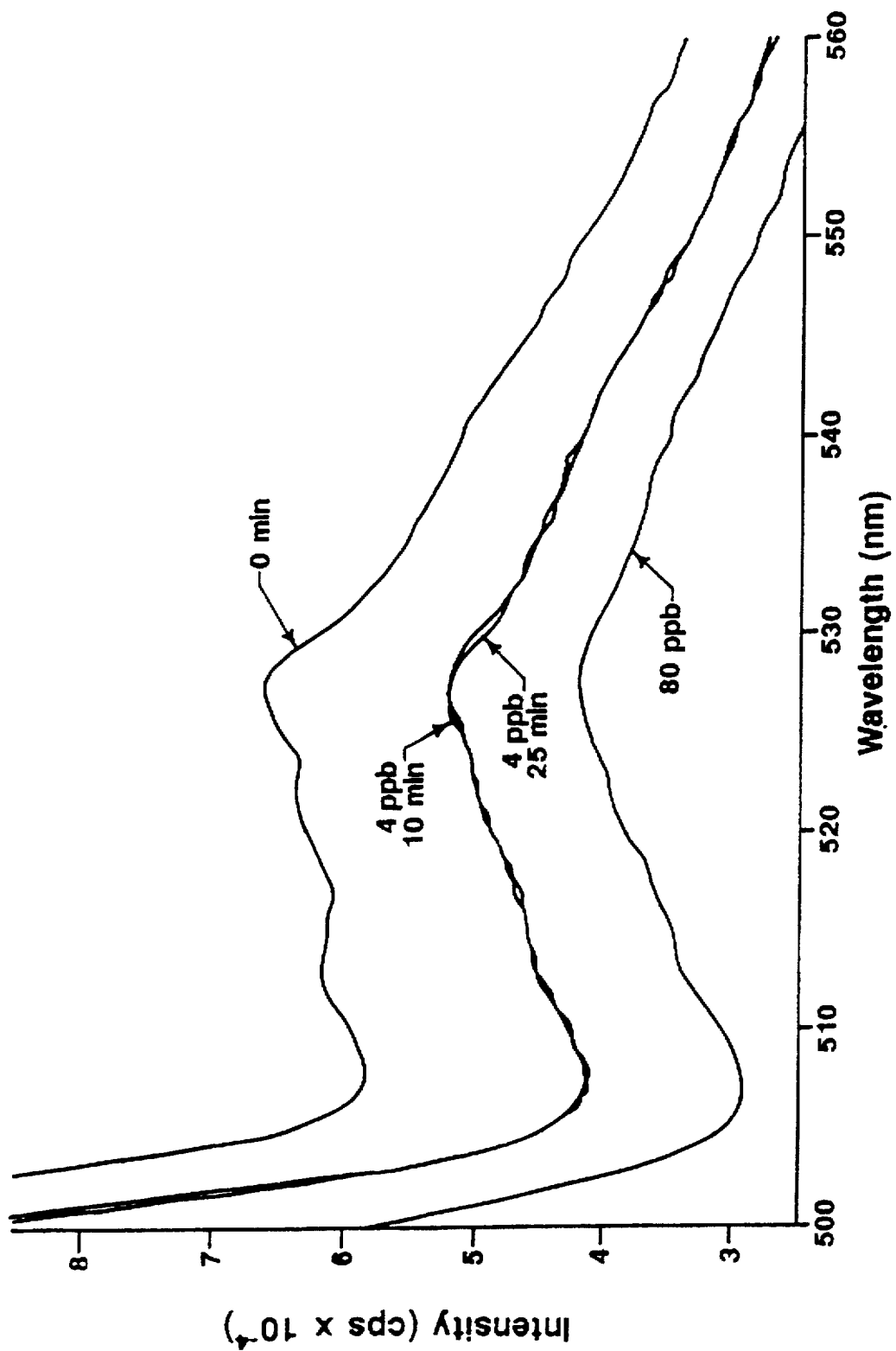
FIG. 12 illustrates the repeatability of 4 ppb cocaine as a function of time.
Figure 13:
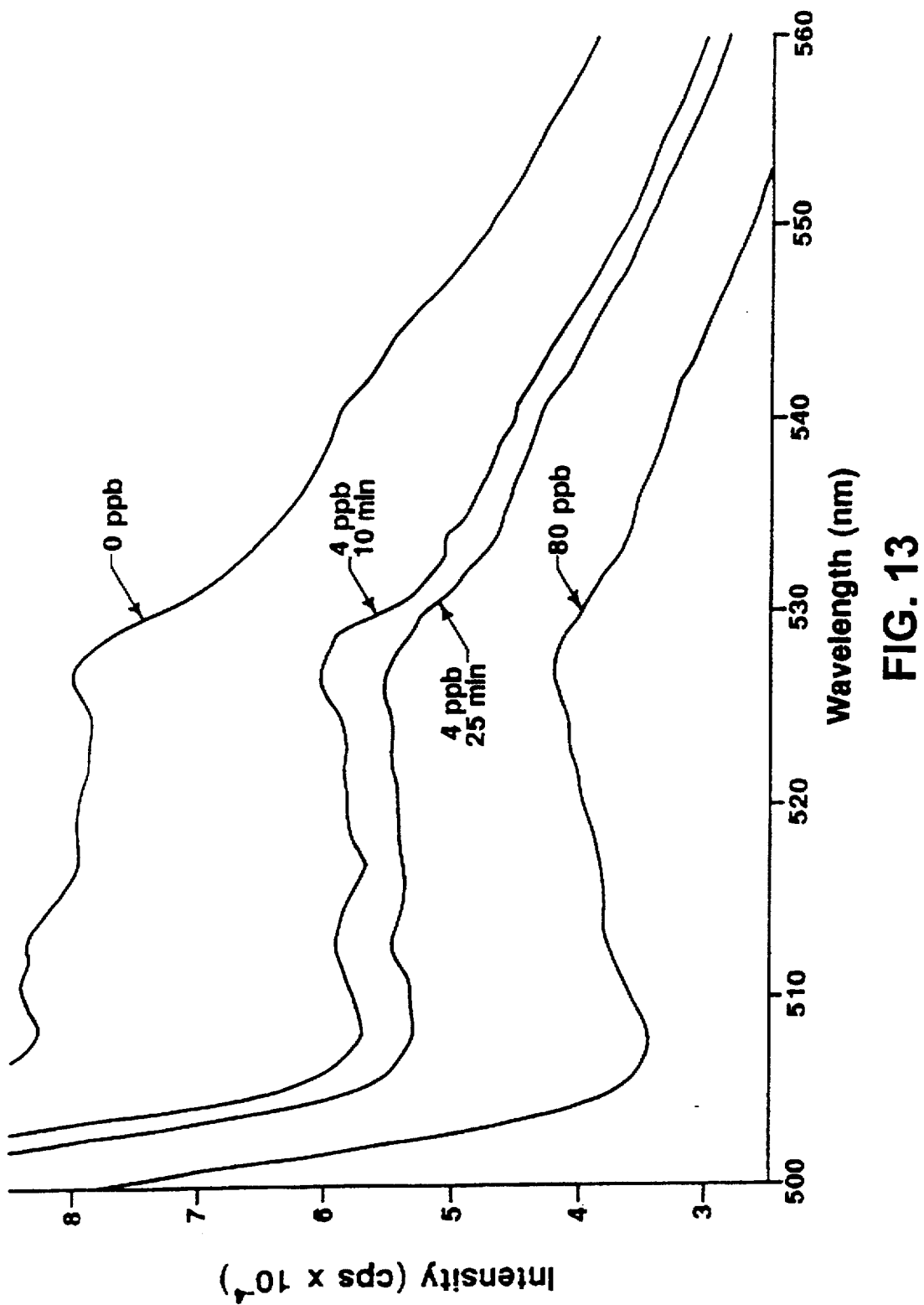
FIG. 13 illustrates the loading effect of a greater amount of antibody-tagged antigen than in FIG. 12.
Figure 14A:
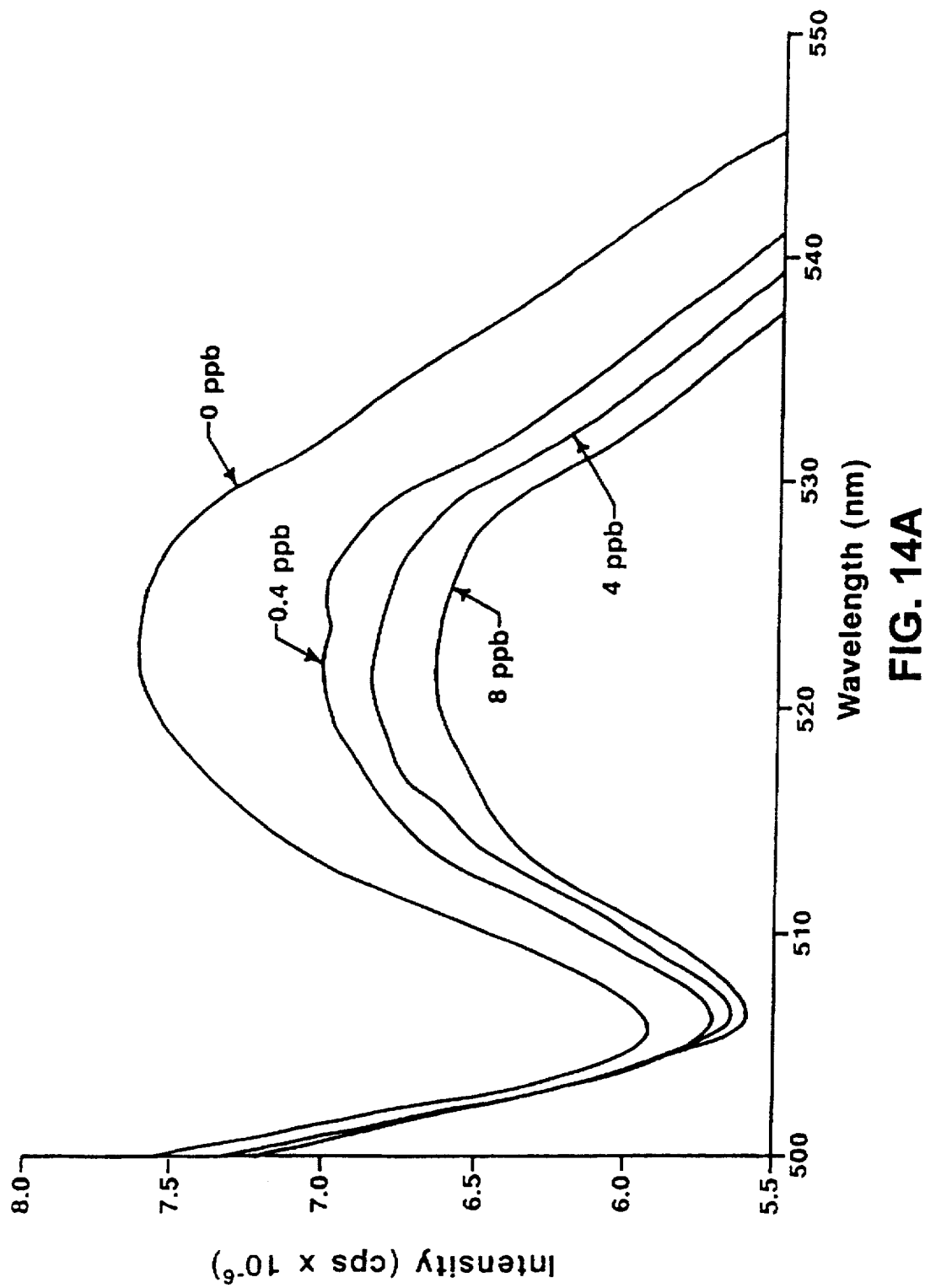
FIG. 14A illustrates detection of a sub-ppb (400 pptr) concentration of cocaine.
Figure 14B:
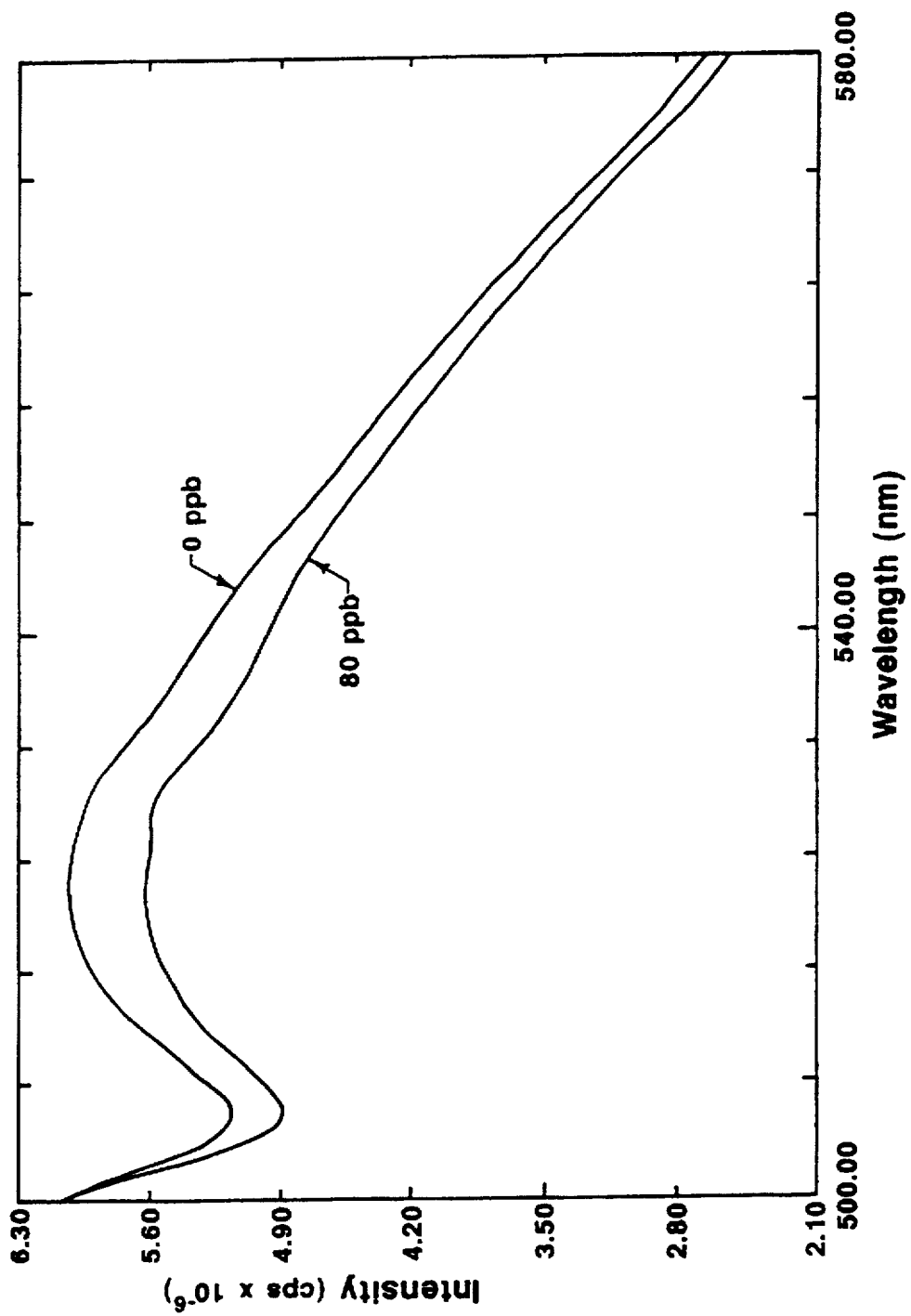
FIG. 14B illustrates detection of sub-ppb (8 pptr) concentration of cocaine using an interference modifier.
Figure 15:
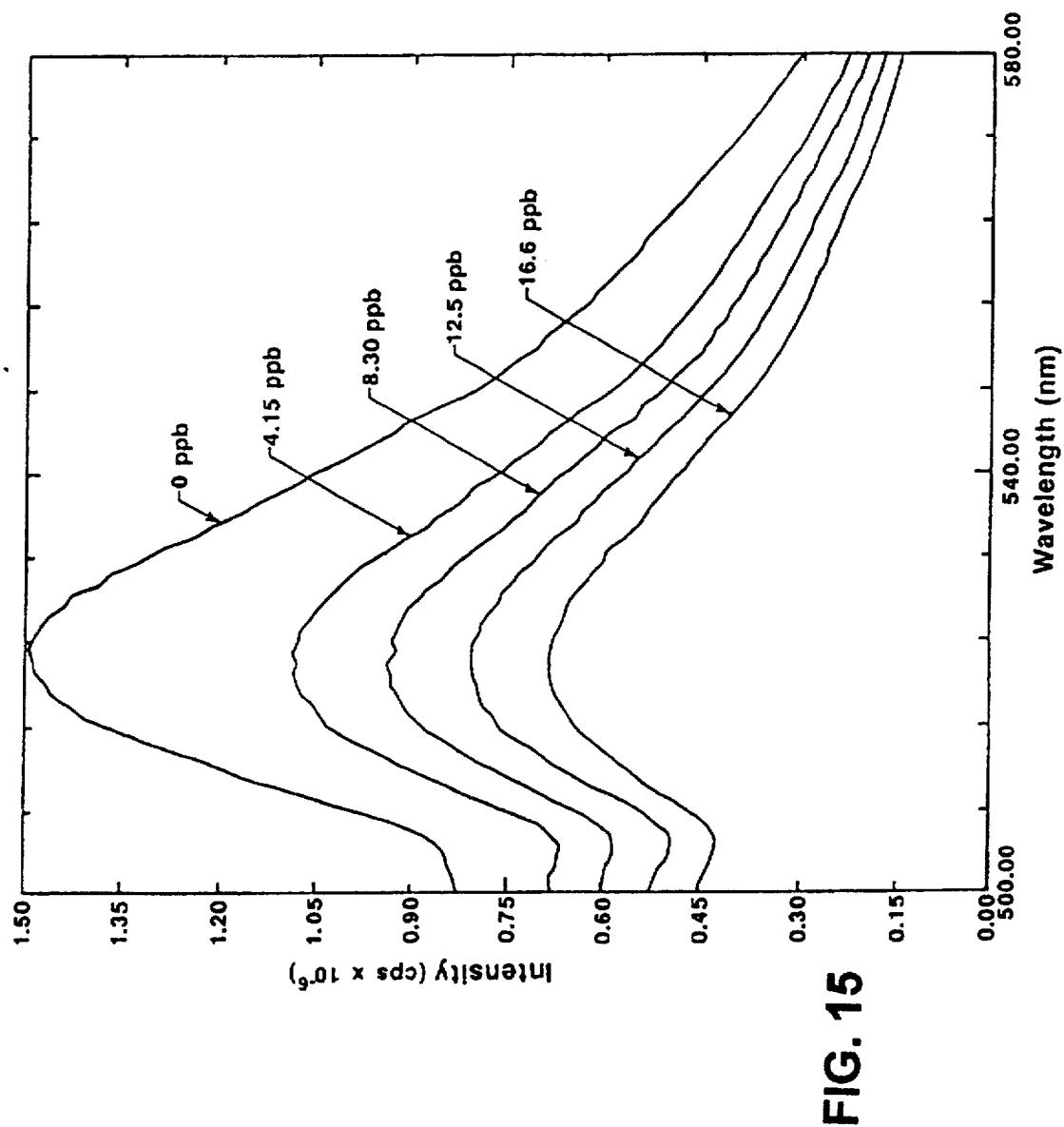
FIG. 15 is the fluorescent spectra of various concentrations of anti-mouse IgG showing its relationship to signal intensity.
Figure 16:
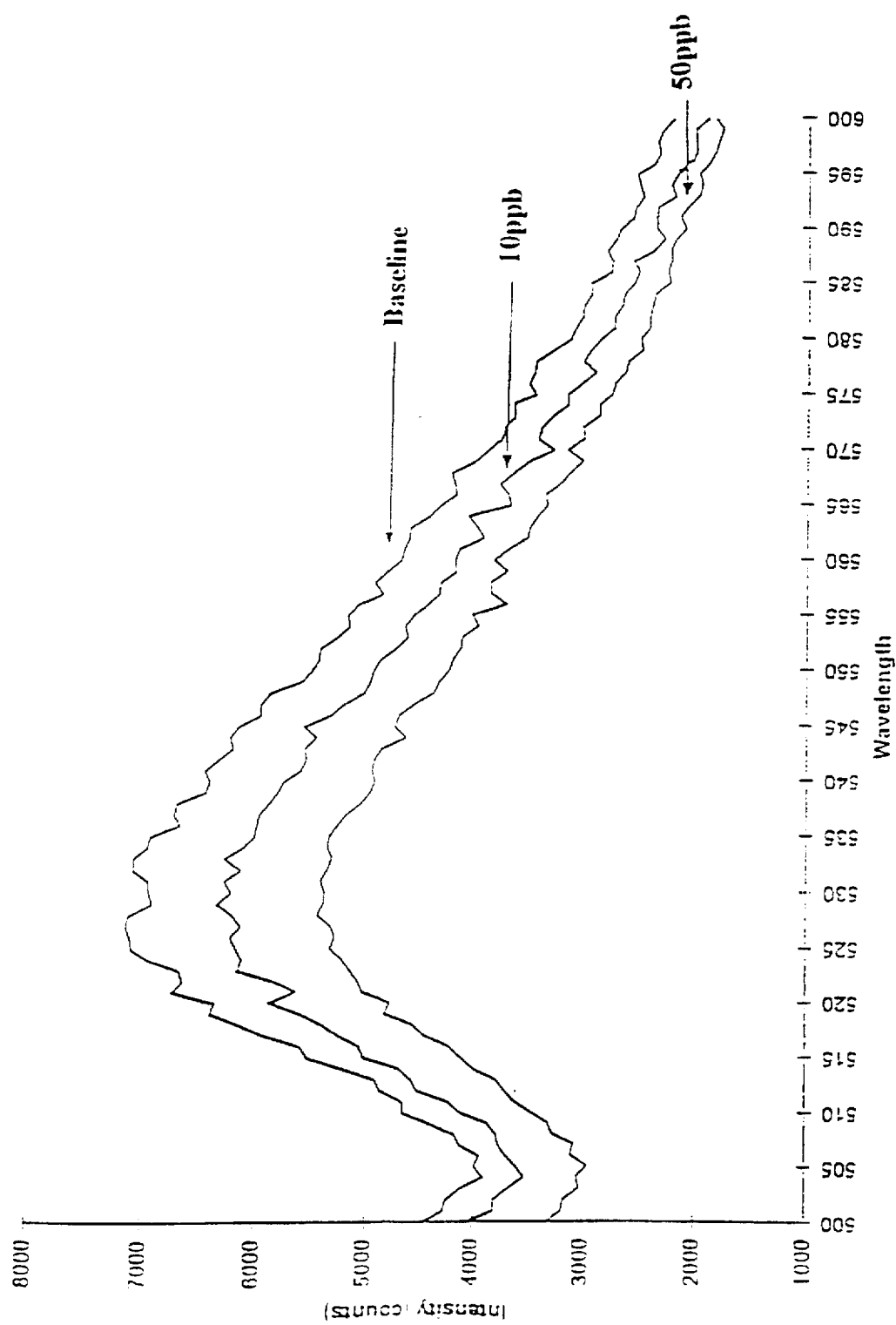
FIG. 16 illustrates the detection of 10 and 50 ppb of atrazine using a membrane substrate.

FIG. 10 shows the improvement that can be made when the above sensitivity improvement methodologies are applied. In this Figure, 4 ppb of cocaine is shown with a signal-to-noise ratio that indicates parts-per-trillion (pptr) sensitivities are attainable. A comparison of FIGS. 9 and 10 shows that in FIG. 9, which used only the improved tag, 160 ppb cocaine produced an intensity change of about 0.2 units while in FIG. 10, which also used the wash, the indestructible antigen-spacer-tag bonds and optical isolation, 4 ppb produces an intensity change of about 1.0 unit. FIG. 11 shows both 4 ppb and 80 ppb. Here it can be seen that the sensor is so sensitive and the exchange rate so efficient that saturation is reached before 80 ppb, i.e., there are not enough tagged sites left and there is no linear relationship between 0.4 and 80 ppb. FIG. 12 shows the repeatability at 4 ppb as a function of time. FIG. 13 shows that there can be a time dependence directly related to the "loading factor" on the substrate. What is important, however, is that the change in counts-per-second (CPS) is the same for both sensors at the ten minute exposure time. At ten minutes, both sensors produced an intensity change of about 2 units for 4 ppb. The difference between FIGS. 12 and 13 is that the substrate in FIG. 13 is "loaded" with more antibody than the substrate in FIG. 12. Over longer time, therefore, more tagged antigen is displaced in FIG. 13 while in FIG. 12 the total amount of tagged antigen is quickly removed. FIG. 14A shows spectra at various cocaine concentrations which demonstrate that very low (pptr) concentrations can be detected. FIG. 14B shows the improvement in sensitivity as a result of using an interference modifier in the tagged antigen; 8 pptr of cocaine are detected, using $(CH_3)_3SiCl$ as the interference modifier with the tag of FIG. 7B. FIG. 15 shows the quantitative aspects of this technology using mouse IgG as the antibody and tagged anti-mouse IgG as the antigen. FIG. 16 shows the response of the solid-state single-step competitive immunoassay sensor to atrazine.

Figure 17:
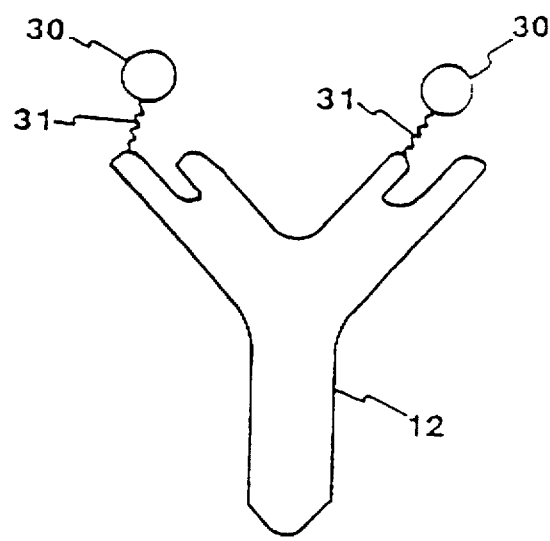
FIG. 17 illustrates a tagged antibody.
Figure 18:
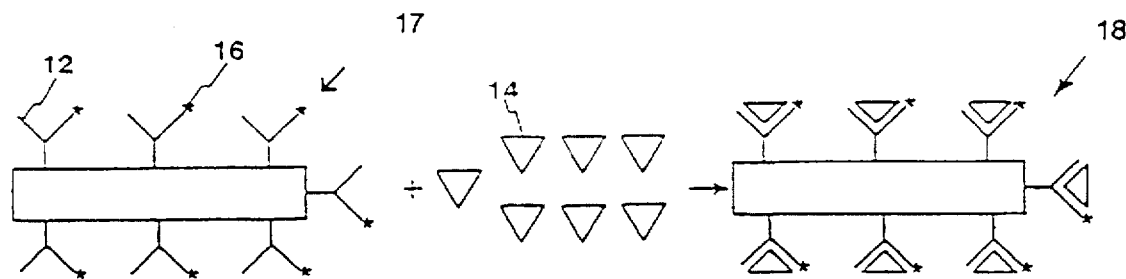
FIG. 18 illustrates the reaction of an immunoassay with tagged antibody.

There are two (2) special cases of solid-state, single-step competitive immunoassay sensors which must be addressed to increase the number of antigens that can be measured: (1) Small molecules where there are active functional groups to attach a tag, but where the tag would distort the antigen to an extent that it would not be recognized by the antibody and (2) Molecules of any size where there are no functional sites to attach the tag. In these cases the tag would have to be put on the antibody. FIG. 17. A suitable tag 30 is attached to antibody 12. If necessary, a long chain high molecular weight compound 31, can be used to accentuate the interaction of the tag with the antigen. The reaction of the immunoassay using tagged antibody is shown in FIG. 18.

Antibody 12 with attached tag 16 is the sensor 17. When this sensor 17 comes in contact with a sample containing target antigen 14, it binds to the tagged antibody, producing an optical change in reacted sensor 18. The optical characteristics of the reacted sensor 18 are a function of the amount of antigen which binds to the tagged antibody. The tag 16 is selected, or attached to antibody 12 in such a manner, so that the sensor 17 has increased sensitivity to antigen 14. The preferred tag is a fluorescent compound but other tags, such as chromophores and radiochemical, will also work.

In the absence of an antigen, the fluorophore attached to the antibody would be free to move around, and therefore, its fluorescence will be highly depolarized. When an antigen binds with the tagged antibody, the movement of the fluorophore becomes restricted, leading to a more polarized luminescence. Polarization measurements, therefore, can be used for quantifying antigens for which a matching tagged antibody is available. The choice of tag is still the key to sensitivity. It should be chosen to give the greatest polarization change and this may be different in each case depending on the antibody and target molecule. The use of a long chain compound for attaching the tag permits greater motion in the absence of antigen, and greater sensitivity in measuring polarization change when antigen binding occurs. Thus, the molecular shape, size and charge distribution, etc. and the method of attachment of the tag can be controlled to produce greater sensitivity of the tagged antibody to the antigen and greater change in the measured optical effect.

Another measurement technique that can also be used involves the use of a fluorescence tag and the modulation of fluorescence lifetimes. This is a different approach than the routine relationship of antigen concentration to light intensity that has been previously described. Lifetime modulation is very specific to the presence of the target molecule sought. Fluorescence lifetime is controlled by the manner of binding the fluorophore to the antibody and how this is affected by the addition of the antigen. Nominally, fluorescent lifetimes in the micro- to nanosecond range have to be measured. This is well within the state of the art, but requires much more sophisticated instrumentation than a direct fluorescence measurement.

Figure 19:
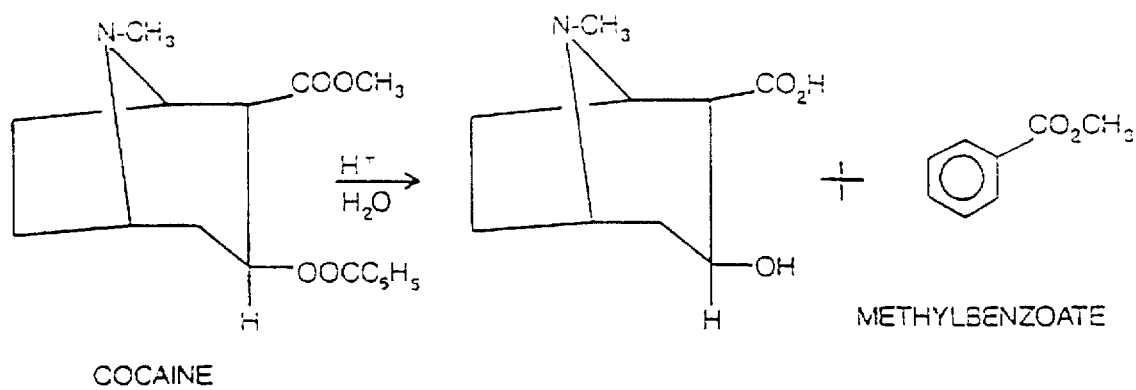
FIG. 19 is the hydrolysis reaction of cocaine resulting in methylbenzoate.

An illustrative example of the tagged antibody process is an alternative method for detecting cocaine. Although cocaine can be detected directly, as shown previously, using a suitable tag and antibody specific to cocaine, with great sensitivity, an indirect approach can also be used. Cocaine and its hydrochloride have very low volatility at ambient conditions. Thus, an alternate approach is to focus on a cocaine derivative having a far greater volatility which will give a higher sample concentration and be easier to detect. When cocaine is shipped, stored or transported, environmental conditions cause degradation. Temperature, humidity, pressure and other environmental variations lead to the production of cocaine derivatives. One of these derivatives (which is always found) is methylbenzoate, a transesterification product formed during the hydrolysis of cocaine, as shown in FIG. 19. Methylbenzoate constitutes a good chemical marker for cocaine, since it is liquid at room temperature and, therefore, has a significantly higher vapor pressure. However, methylbenzoate is a small molecule, devoid of functionalities that could be used for tagging with a fluorophore. Therefore, the antibody is tagged with a fluorophore. Polarization measurements for quantifying methylbenzoate can be made and can be directly related to the presence of cocaine.

The approaches introduced can also be applied to the use of multiple sensors on a single substrate. This is accomplished by simply changing the tag while applying all of the other enhancement parameters. The first step is to use antibodies which are specific to each of the antigens (target molecules) of interest. The next stage is to select different tags for each antigen or antibody. When fluorescence tags are used: (1) They must have an active group where attachment can take place, (2) They must have very high quantum efficiency and (3) They must each have a distinctive spectral property. Simplicity is added to the total system if these fluorophores excite at the same wavelength and emit at well-separated different wavelengths. Fluorescein and rhodamine are a pair of the better choices because they meet these criteria. For example, a multiple sensor for morphine and cocaine can be made using the antibodies specific to each of these and tagging the antigens differently, i.e., one with a fluorescein compound and the other with a rhodamine compound. This concept can be extended to several sensors on a single substrate by choosing additional tags. The best way to accomplish this is to mask the substrate into as many sections as there are antibodies and immobilize these individually. The use of antibody mixtures, in exactly known concentration mixes, does not assure that these will be attached to the substrate in these ratios or that the relationship between these will be the same from sensor to sensor. Each tag will have its own specific emission wavelength which means there will have to be a fixed spectral channel for each of these or a tunable detection system.

The fluorescence tagged analyte competition approach described herein focuses on simplicity, storage and operational life, sensitivity and the ability to get quantitative data. The sensor provides one step operation:

1) The sensor comes in contact with the analyte and this replaces the tagged site effeciently because affinity control makes the antibody-untagged analyte the preferred configuration.

2) This results in a loss of fluorescence which is proportional to sample concentration (the light path is through the thin biochemistry film and this obviates any adverse background contributions).

Changes and modifications in the specifically described embodiments can be carried out without departing from the scope of the invention which is intended to be limited only the scope of the appended claims.

We claim:

1. A solid state competitive immunoassay sensor for detecting the presence of a particular analyte, comprising:
    a solid substrate which transmits light;
    an antibody to which the analyte binds immobilized on the solid substrate;
    an affinity controlled tagged form of the analyte displaceably bound to the antibody and having a lower binding energy to the antibody than untagged analyte, wherein untagged analyte will displace tagged analyte and bind to the antibody when the antibody with tagged analyte contacts a sample containing untagged analyte, the antibody with bound tagged analyte having an optical property which is changed by displacement of tagged analyte by untagged analyte, the antibody with bound tagged analyte forming a solid state system, the affinity controlled tagged form of the analyte having a binding energy to the antibody to provide a desired level of sensitivity to the untagged analyte, the affinity controlled tagged form of the analyte including an interference modifier which removes displaced tagged analyte from the field of view of the sensor.

2. The sensor of claim 1 further comprising an optical detector positioned with respect to the solid substrate to detect changes in the optical property produced by displacement of the tagged analyte by untagged analyte.

3. The sensor of claim 1 wherein the affinity controlled tagged form of the analyte comprises the analyte A, an active indicator T, an affinity controller component Y and an interference modifier component M, bound together to form a single entity A-T-Y-M.

4. The sensor of claim 1 wherein the interference modifier is a component which volatilizes the displaced tagged analyte.

5. The sensor of claim 4 wherein the interference modifier is a trimethyl silyl compound.

6. The sensor of claim 1 wherein the interference modifier is a component which has a site which binds to a surface of the sensor.

7. The sensor of claim 6 wherein the interference modifier contains the moiety —Cl.

8. The sensor of claim 1 wherein the affinity controlled tagged analyte is selected on the basis of any of size, shape, molecular weight, and chain length.

9. The sensor of claim 1 wherein the solid substrate is a membrane, a waveguide, or a container.

10. The sensor of claim 1 further comprising an optical isolation layer on the solid substrate.

11. The sensor of claim 1 wherein the antibody immobilized to the solid substrate is substantially saturated with tagged analyte.

12. The sensor of claim 3 wherein the active indicator is a fluorophore or a chromophore.

13. The sensor of claim 1 further comprising a gel layer surrounding or in intimate contact with the immobilized antibody with bound tagged analyte, the gel layer being permeable to the untagged analyte.

14. A solid state competitive immunoassay sensor for detecting the presence of a particular analyte, comprising:
    a solid substrate which transmits light;
    an antibody to which the analyte binds immobilized on the solid substrate;
    an affinity controlled tagged form of the analyte displaceably bound to the antibody and having a lower binding energy to the antibody than untagged analyte, wherein untagged analyte will displace tagged analyte and bind to the antibody when the antibody with tagged analyte contacts a sample containing untagged analyte, the antibody with bound tagged analyte having an optical property which is changed by displacement of tagged analyte by untagged analyte, the antibody with bound tagged analyte forming a solid state system, the affinity controlled tagged form of the analyte having a binding energy to the antibody to provide a desired level of sensitivity to the untagged analyte;

a gel layer surrounding or in intimate contact with the immobilized antibody with bound tagged analyte to provide an internal wet environment around the immobilized antibody with bound tagged analyte, the gel layer being permeable to the untagged analyte.

15. The sensor of claim 14 further comprising an optical detector positioned with respect to the solid substrate to detect changes in the optical property produced by displacement of the tagged analyte by untagged analyte.

16. The sensor of claim 1 wherein the affinity controlled tagged form of the analyte comprises the analyte A, an active indicator T, and an affinity controller X, bound together to form a single entity A-T-X.

17. The sensor of claim 16 wherein the affinity controller X comprises an affinity controller component Y and an interference modifier component M to form a tagged analyte A-T-Y-M.

18. The sensor of claim 14 wherein the gel layer comprises an aqua-gel or a sol-gel.

19. The sensor of claim 14 wherein the gel layer comprises a plurality of gel beads which encapsulate a fluid.

20. The sensor of claim 19 wherein the fluid is selected from water, a buffer, or a solvent.

21. The sensor of claim 19 wherein the gel beads are sufficiently porous to provide a continuous controlled leakage of encapsulated fluid to the immobilized antibody with bound tagged analyte.

22. The sensor of claim 19 wherein the gel beads are substantially nonporous and do not provide the encapsulated fluid to the immobilized antibody with bound tagged antigen until crushed by the application of external pressure to release the fluid.

23. The sensor of claim 19 wherein the gel beads are mixed or interspersed with the immobilized antibody with bound tagged analyte.

24. The sensor of claim 19 wherein the gel beads are above and/or below the immobilized antibody with bound tagged analyte.

25. The sensor of claim 14 wherein the solid substrate is a membrane, a waveguide, or a container.

26. The sensor of claim 14 further comprising a protective layer on the gel layer.

27. A solid state sensor for detecting the presence of a particular analyte which cannot be tagged for detection by a competitive immunoassay, comprising:

a solid substrate which transmits light;

an affinity controlled tagged antibody to which the analyte binds immobilized on the solid substrate, wherein analyte will bind to the tagged antibody when the tagged antibody contacts a sample containing the analyte, the tagged antibody having an optical property which is changed when analyte binds to the tagged antibody, the affinity controlled tagged antibody having a binding energy for the analyte to provide a desired level of sensitivity to the analyte;

a gel layer surrounding or in intimate contact with the immobilized affinity controlled tagged antibody to provide an internal wet environment around the immobilized tagged antibody, the gel layer being permeable to the analyte.

28. The sensor of claim 27 further comprising an optical detector positioned with respect to the solid substrate to detect changes in the optical property produced by binding of the analyte to the tagged antibody.

29. The sensor of claim 27 wherein the affinity controlled tagged antibody comprises an antibody, an active indicator, and an affinity controller, bound together to form a single entity.

30. The sensor of claim 27 wherein the gel layer comprises an aqua-gel or a sol-gel.

31. The sensor of claim 27 wherein the solid substrate is a membrane, a waveguide, or a test tube, cuvette, bottle or other container.

32. The sensor of claim 27 wherein the gel layer comprises a plurality of gel beads which encapsulate a fluid.

* * * * *